United States Patent
Graham et al.

(10) Patent No.: US 10,426,546 B2
(45) Date of Patent: Oct. 1, 2019

(54) LAPAROSCOPIC HANDPIECE FOR WAVEGUIDES

(71) Applicant: OMNIGUIDE, INC., Lexington, MA (US)

(72) Inventors: Marc Graham, Somerville, MA (US); Arnaz Singh Malhi, Watertown, MA (US); Vladimir Fuflyigin, Medford, MA (US); Courtney Manthei Sienkowski, Beacon Falls, CT (US); Flora Liu, Boston, MA (US)

(*) Notice: Subject to any disclaimer, the term of this patent is extended or adjusted under 35 U.S.C. 154(b) by 0 days.

(21) Appl. No.: 15/512,226

(22) PCT Filed: Sep. 17, 2015

(86) PCT No.: PCT/US2015/050773
§ 371 (c)(1),
(2) Date: Mar. 17, 2017

(87) PCT Pub. No.: WO2016/044640
PCT Pub. Date: Mar. 14, 2016

(65) Prior Publication Data
US 2017/0245933 A1 Aug. 31, 2017

Related U.S. Application Data

(60) Provisional application No. 62/052,409, filed on Sep. 18, 2014.

(51) Int. Cl.
*A61B 18/22* (2006.01)
*A61B 1/008* (2006.01)
(Continued)

(52) U.S. Cl.
CPC .............. *A61B 18/22* (2013.01); *A61B 1/008* (2013.01); *A61B 1/0052* (2013.01); *A61B 1/313* (2013.01);
(Continued)

(58) Field of Classification Search
CPC ... A61B 18/22; A61B 17/00234; A61B 17/29; A61B 17/320016; A61B 2017/00314;
(Continued)

(56) References Cited

U.S. PATENT DOCUMENTS 4,641,657 A * 2/1987 Ellis .................. A61B 8/06
600/459
5,107,709 A * 4/1992 McCarty .............. G01N 29/221
73/655
(Continued)

FOREIGN PATENT DOCUMENTS

EP 2 263 568 A2 12/2010
EP 2 594 211 A1 5/2013
(Continued)

OTHER PUBLICATIONS

Extended European Search Report, dated Mar. 21, 2018, for European Application No. 15842019.0-1124, 9 pages.
(Continued)

*Primary Examiner* — Carl H Layno
*Assistant Examiner* — Michael J Lau
(74) *Attorney, Agent, or Firm* — Cozen O'Connor

(57) ABSTRACT

An articulating instrument including a distal assembly having first and second configurations and intermediate configurations between them. At least one of the first and second configurations is substantially stable such that the distal assembly of the instrument has a tendency to remain in the stable configuration when placed in that configuration by a user of the instrument. Preferably, the distal assembly terminates in a distal tip unit defining at least one distal feature that is useful for manipulating tissue.

15 Claims, 20 Drawing Sheets

(51) Int. Cl.
| | |
|---|---|
| *A61B 1/313* | (2006.01) |
| *A61B 17/29* | (2006.01) |
| *A61B 1/005* | (2006.01) |
| *A61B 17/32* | (2006.01) |
| *A61B 17/00* | (2006.01) |
| *A61B 18/14* | (2006.01) |
| *A61B 18/20* | (2006.01) |
| *A61B 18/00* | (2006.01) |

(52) U.S. Cl.
CPC ........ *A61B 17/00234* (2013.01); *A61B 17/29* (2013.01); *A61B 17/320016* (2013.01); *A61B 18/14* (2013.01); *A61B 18/1445* (2013.01); *A61B 18/1482* (2013.01); *A61B 18/201* (2013.01); *A61B 2017/00314* (2013.01); *A61B 2017/00327* (2013.01); *A61B 2017/00469* (2013.01); *A61B 2017/2905* (2013.01); *A61B 2017/320044* (2013.01); *A61B 2018/00577* (2013.01); *A61B 2018/00601* (2013.01); *A61B 2018/00642* (2013.01); *A61B 2018/2255* (2013.01)

(58) Field of Classification Search
CPC   A61B 2017/00327; A61B 2017/00469; A61B 2017/2905; A61B 2017/320044; A61B 2018/2255; A61B 2018/2285; G01M 11/37
USPC .................. 606/17, 19, 45, 46, 47, 263, 107
See application file for complete search history.

(56) References Cited

U.S. PATENT DOCUMENTS

| | | | | |
|---|---|---|---|---|
| 5,346,504 | A * | 9/1994 | Ortiz | A61B 34/70 600/116 |
| 5,420,882 | A * | 5/1995 | Black | B23K 26/0604 372/107 |
| 5,440,664 | A * | 8/1995 | Harrington | G02B 6/032 385/125 |
| 5,448,989 | A * | 9/1995 | Heckele | A61B 1/0055 600/104 |
| 5,454,827 | A * | 10/1995 | Aust | A61B 17/29 600/564 |
| 5,467,763 | A * | 11/1995 | McMahon | A61B 17/00234 600/201 |
| 5,478,003 | A * | 12/1995 | Green | A61B 17/07207 227/176.1 |
| 5,540,706 | A * | 7/1996 | Aust | A61B 17/32002 606/170 |
| 5,951,543 | A * | 9/1999 | Brauer | A61B 18/201 606/10 |
| 5,954,638 | A | 9/1999 | Spranza, III | |
| 6,130,780 | A | 10/2000 | Joannopoulos et al. | |
| 6,463,200 | B2 | 10/2002 | Fink et al. | |
| 6,788,864 | B2 | 9/2004 | Ahmad et al. | |
| 6,801,698 | B2 | 10/2004 | King et al. | |
| 6,887,233 | B2 * | 5/2005 | Angeley | A61B 18/203 606/10 |
| 6,898,359 | B2 | 5/2005 | Soljacic et al. | |
| 7,142,756 | B2 | 11/2006 | Anderson et al. | |
| 7,167,622 | B2 | 1/2007 | Temelkuran et al. | |
| 7,272,285 | B2 | 9/2007 | Benoit et al. | |
| 7,295,734 | B2 | 11/2007 | Bayindir et al. | |
| 7,311,962 | B2 | 12/2007 | Fink et al. | |
| 7,331,954 | B2 | 2/2008 | Temelkuran et al. | |
| 8,075,476 | B2 | 12/2011 | Vargas | |
| 8,280,212 | B2 | 10/2012 | Goell et al. | |
| 8,517,933 | B2 | 8/2013 | Mohr | |
| 9,220,559 | B2 * | 12/2015 | Worrell | A61B 18/1445 |
| 9,775,669 | B2 * | 10/2017 | Marczyk | A61B 17/29 |
| 9,883,880 | B2 * | 2/2018 | Malkowski | A61B 17/29 |
| 2006/0052661 | A1 | 3/2006 | Gannot et al. | |
| 2006/0199999 | A1 * | 9/2006 | Ikeda | A61B 1/00149 600/141 |
| 2008/0058595 | A1 * | 3/2008 | Snoke | A61B 1/00135 600/114 |
| 2008/0249483 | A1 | 10/2008 | Slenker et al. | |
| 2009/0171332 | A1 | 7/2009 | Bonneau | |
| 2009/0171372 | A1 | 7/2009 | Mohr | |
| 2009/0248041 | A1 | 10/2009 | Williams et al. | |
| 2009/0299352 | A1 * | 12/2009 | Zerfas | A61B 1/00165 606/15 |
| 2010/0010512 | A1 * | 1/2010 | Taylor | A61B 17/04 606/144 |
| 2010/0249507 | A1 | 9/2010 | Prisco et al. | |
| 2011/0009863 | A1 * | 1/2011 | Marczyk | A61B 18/1445 606/51 |
| 2011/0106078 | A1 | 5/2011 | Mueller | |
| 2011/0213363 | A1 * | 9/2011 | Cunningham | A61B 18/1445 606/41 |
| 2011/0230875 | A1 * | 9/2011 | Walberg | A61B 17/29 606/33 |
| 2012/0010616 | A1 * | 1/2012 | Huang | A61B 18/1445 606/52 |
| 2012/0109186 | A1 * | 5/2012 | Parrott | A61B 17/29 606/206 |
| 2012/0215234 | A1 * | 8/2012 | Chowaniec | A61B 17/0469 606/144 |
| 2012/0253326 | A1 * | 10/2012 | Kleyman | A61B 34/71 606/1 |
| 2013/0064515 | A1 * | 3/2013 | Shurgalin | A61B 18/22 385/125 |
| 2013/0123783 | A1 * | 5/2013 | Marczyk | A61B 17/29 606/45 |
| 2013/0131649 | A1 * | 5/2013 | Hughett, Sr. | A61B 17/1227 606/1 |
| 2013/0190562 | A1 * | 7/2013 | Smith | A61B 1/018 600/107 |
| 2013/0253489 | A1 * | 9/2013 | Nau, Jr. | A61B 18/22 606/16 |
| 2013/0281924 | A1 * | 10/2013 | Shellenberger | A61B 17/00234 604/95.01 |
| 2014/0088577 | A1 * | 3/2014 | Anastassiou | A61B 18/201 606/17 |
| 2014/0316395 | A1 * | 10/2014 | Shurgalin | A61B 18/22 606/13 |

FOREIGN PATENT DOCUMENTS

| | | | | |
|---|---|---|---|---|
| EP | 3193695 | A1 * | 7/2017 | ..... A61B 17/320016 |
| SU | 484866 | A1 | 9/1975 | |
| SU | 938967 | A1 | 6/1982 | |
| WO | 2006/135701 | A2 | 12/2006 | |
| WO | 2008/045348 | A2 | 4/2008 | |
| WO | 2011/005335 | A1 | 1/2011 | |
| WO | 2013/192431 | A1 | 12/2013 | |
| WO | 2014/143688 | A2 | 9/2014 | |
| WO | WO-2016044640 | A1 * | 3/2016 | ..... A61B 17/320016 |

OTHER PUBLICATIONS

Fuflyigin et al., "System and Method to Control Surgical Energy Devices," U.S. Appl. No. 61/929,343, filed Jan. 20, 2014, 43 pages.
International Search Report for PCT/US2015/050773, completed Dec. 2, 2015, 2 pages.
Written Opinion for PCT/US2015/050773, completed Dec. 2, 2015, 4 pages.

* cited by examiner

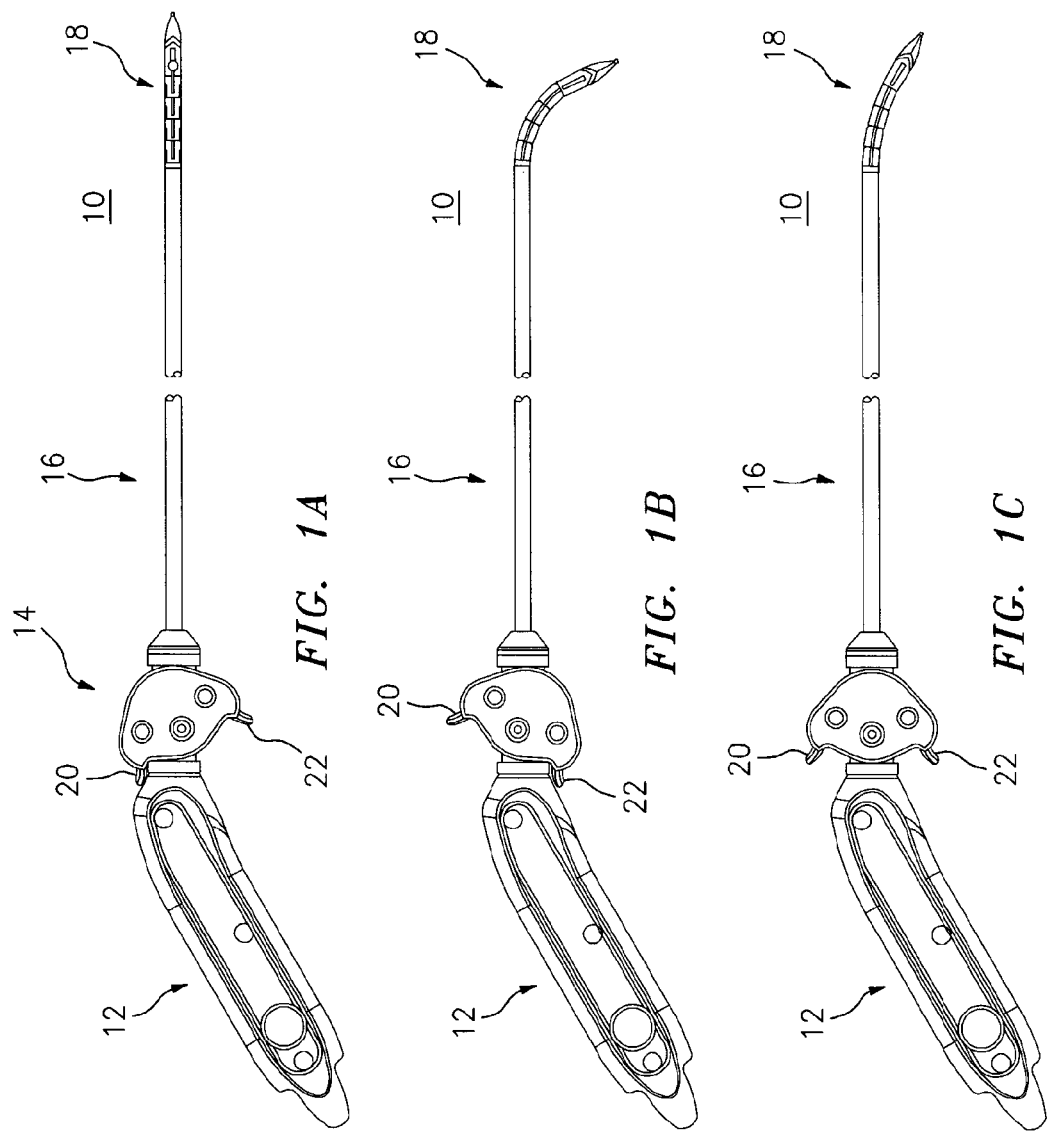

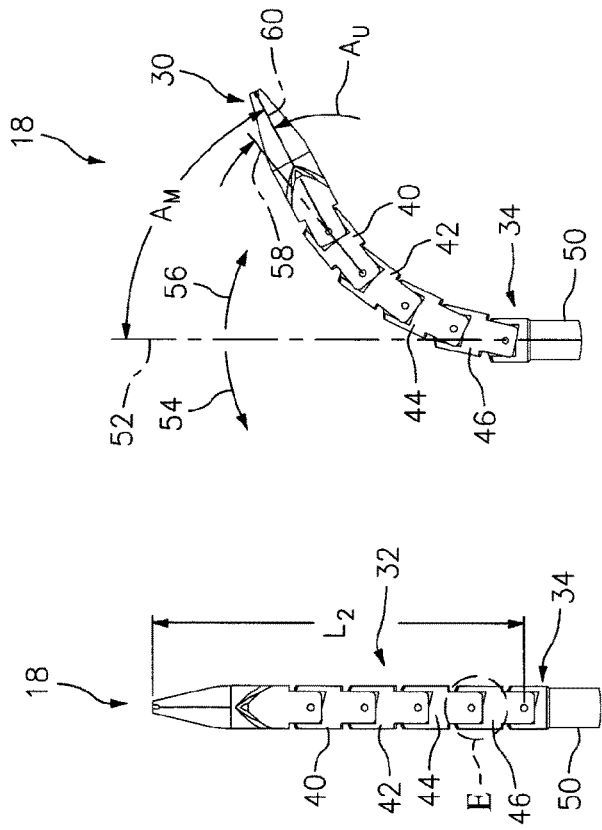
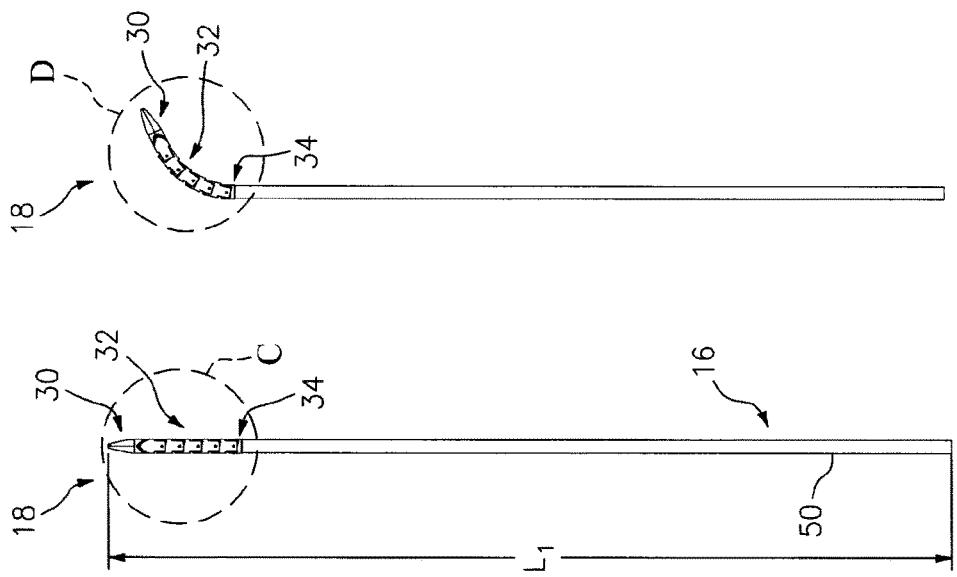
FIG. 2A  FIG. 2B  FIG. 2C  FIG. 2D  FIG. 2E

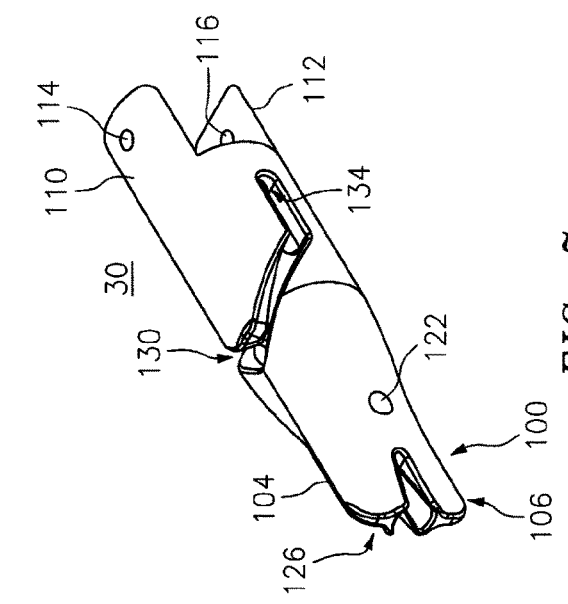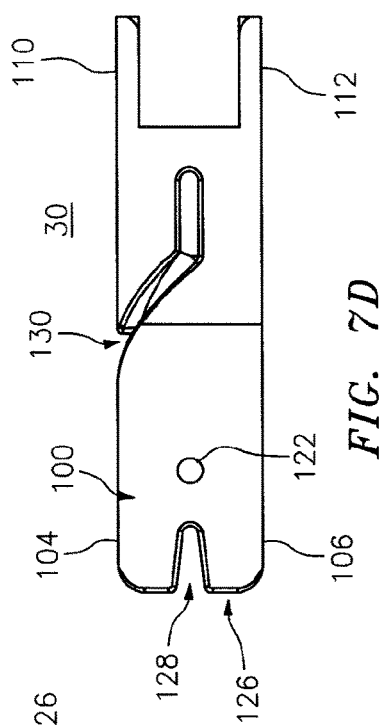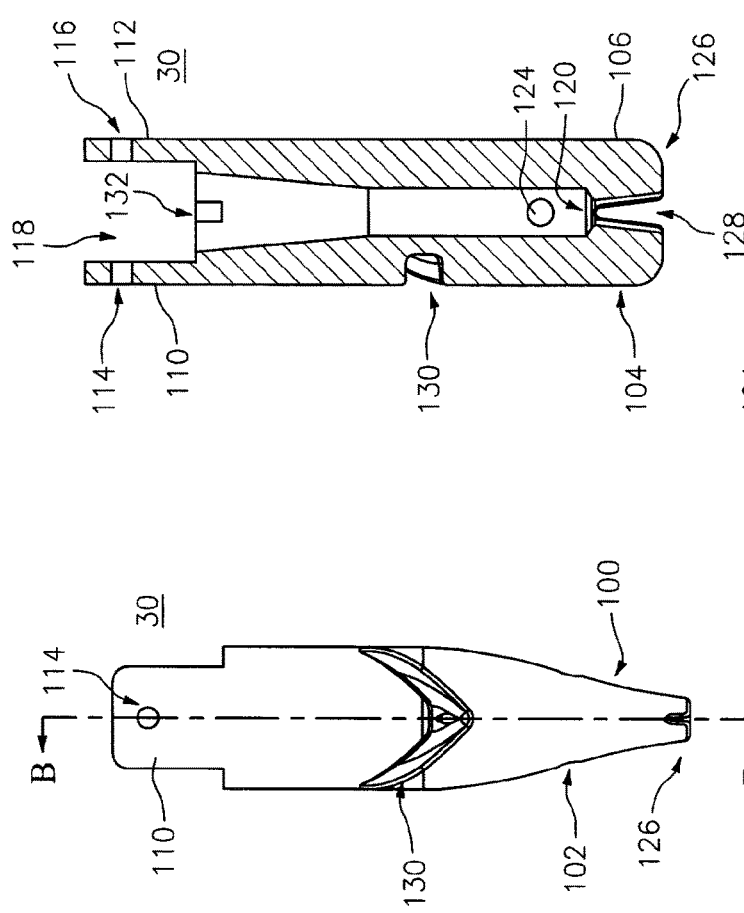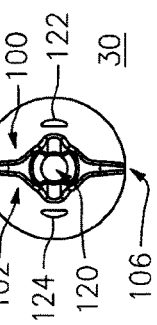

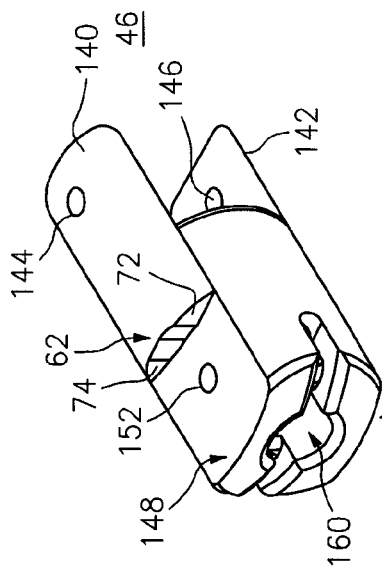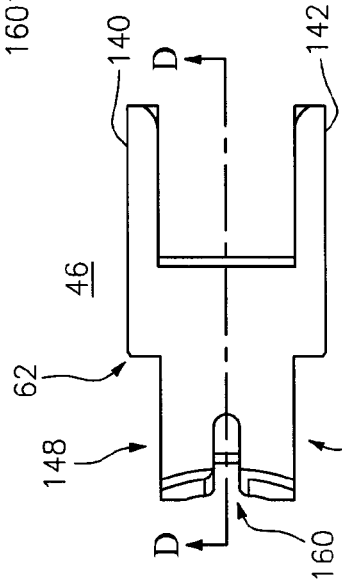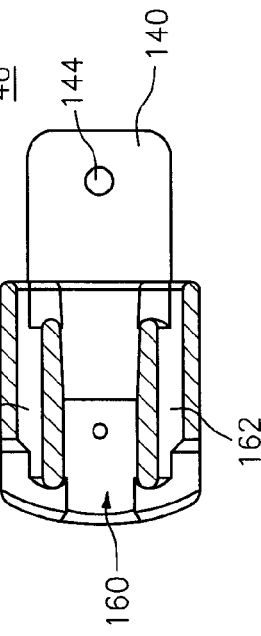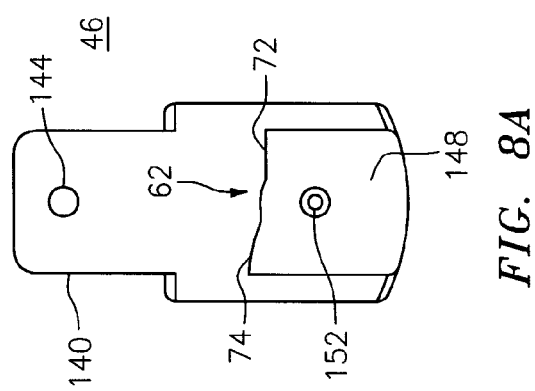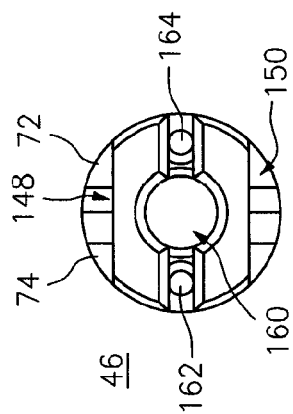

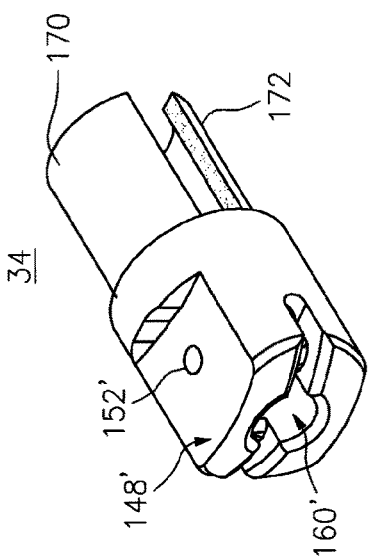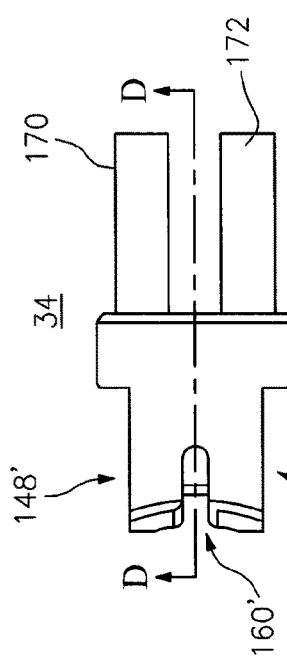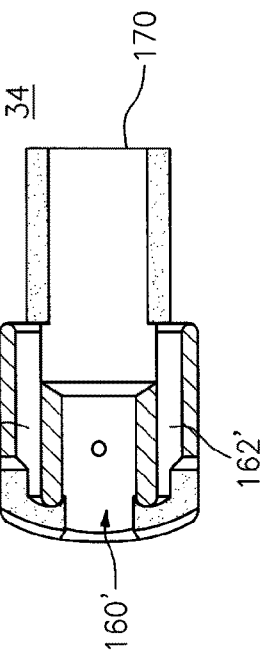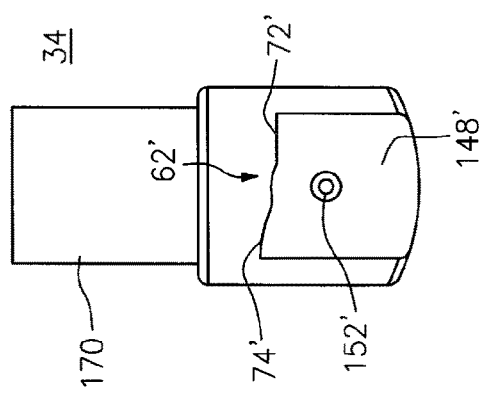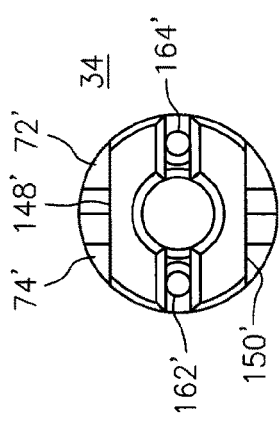

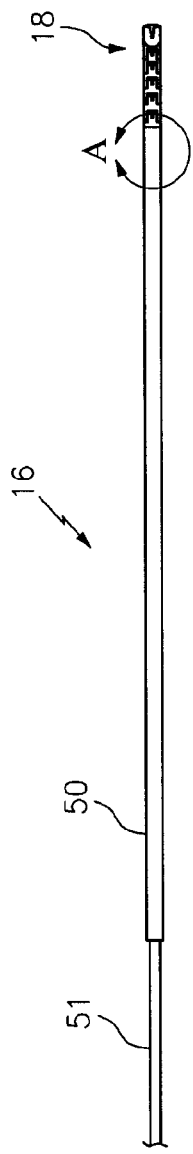
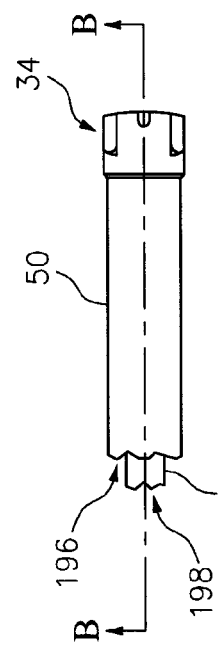
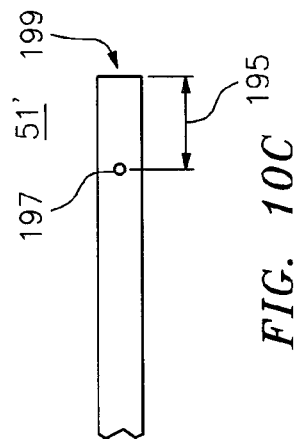
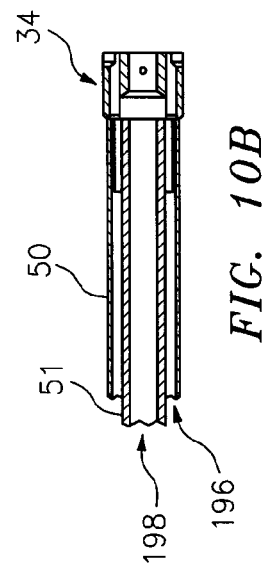

LAPAROSCOPIC HANDPIECE FOR WAVEGUIDES

CROSS-REFERENCE TO RELATED APPLICATION

This application claims priority to U.S. Provisional Application No. 62/052,409 filed 18 Sep. 2014.

FIELD OF THE INVENTION

The invention relates to articulating laparoscopic instruments and more particularly to reusable handpieces for waveguides.

BACKGROUND OF THE INVENTION

There are a number of surgical devices utilized by surgeons that deliver one or more types of energy to cut, coagulate, ablate, remove or otherwise treat tissue of a patient. Surgical energy devices include ultrasonic devices, electrosurgical devices utilizing monopolar and/or bipolar RF (Radio-Frequency) current, microwave and/or thermal energy devices, and higher-frequency electromagnetic radiation delivery devices such as lasers. Such surgical energy devices are utilized by themselves in some surgical techniques and, in other techniques, are utilized in combination with one or more other tools such as forceps or graspers.

Examples of medical laser systems utilizing hollow waveguides are provided by Temelkuran et al. in U.S. Pat. Nos. 7,167,622 and 7,331,954, and by Goell et al. in U.S. Pat. No. 8,280,212, all assigned to OmniGuide, Inc. of Cambridge, Mass. For sterility, safety and quality assurance purposes, each waveguide is utilized for only a single surgical procedure. At the beginning of a procedure, a single-use waveguide is inserted into a reusable handpiece which is graspable by a surgeon.

Many surgical instruments have been designed to bend in multiple directions to assist insertion and to manipulate tissue. An intraluminal manipulator is disclosed by Ortiz et al. in U.S. Pat. No. 5,346,504. Arthroscopic and endoscopic instruments with articulating shafts are described by McMahon in U.S. Pat. No. 5,467,763 and by Aust et al. in U.S. Pat. Nos. 5,454,827 and 5,540,706. An instrument with positive and non-positive linking of segments, for insertion into body cavities, is presented by Heckele in U.S. Pat. No. 5,448,989. Articulated and steerable tips of endoscopic devices and cannulas for robotic surgery are disclosed by Bonneau and by Prisco et al. in U.S. Patent Publication Nos. 2009/0171332 and 2010/0249507, respectively, and by Vargas in U.S. Pat. No. 8,075,476, for example.

A difficulty in targeting desired tissue may arise when utilizing a non-visible energy beam such as a $CO_2$ laser beam. Positioning of an ultrasonic beam utilizing one or more light sources is disclosed by McCarty in U.S. Pat. No. 5,107,709. It is also known to align non-visible laser beams utilizing phosphor screens available from LUMITEK International, Inc. of Ijamsville, Md., especially for bench testing and research purposes. Visible aiming beams utilized with $CO_2$ lasers are described by Michael Black in U.S. Pat. No. 5,420,882, by Temelkuran et al. in U.S. Pat. No. 7,331,954, by Shapira et al. in WO2006/135701 and by Gannot et al. in U.S. Patent Publication No. 2006/0052661, for example. However, there remains a need to optimize tissue treatment under actual conditions which may vary from patient to patient, and may vary among different tissues and locations within each patient.

It is therefore desirable to have an improved system and method to effectively access and treat selected tissue within a patient utilizing surgical energy devices.

SUMMARY OF THE INVENTION

An object of the present invention is to provide an improved articulating instrument for surgical procedures utilizing surgical energy.

Another object of the present invention is to provide such an instrument which is also useful for manipulating tissue.

A still further object of the present invention is to provide such an instrument which can readily accept and protect single-use waveguides during surgical procedures.

Yet another object of the present invention is to provide such an instrument which can assist aiming and/or orientation of its distal tip utilizing one or more physical features.

This invention features an articulating instrument including a handle with an articulation actuator, a cannula portion, and a distal assembly terminating in a distal tip unit and having (1) a first configuration that is substantially straight or at a first curved orientation, (2) a second configuration at a second curved orientation, and (3) variable intermediate configurations between the first and second configurations. At least one of the first and second configurations is substantially stable such that the distal assembly of the instrument has a tendency to remain in the stable configuration when placed in that configuration by a user of the instrument. The cannula portion connects the distal assembly with the handle and contains at least one actuation member having a proximal end connected to the actuator and having a distal portion associated with, such as connected to, the distal tip unit. Preferably, the distal tip unit defines at least one distal feature that is useful for manipulating tissue.

In various embodiments, the distal assembly includes a plurality of links that are pivotally interconnected. Preferably, the links have shoulders that serve as hard stops to limit the amount of articulation.

In a number of embodiments, the actuation member is a cable having a central portion passing through the distal tip unit and having first and second cable legs that extend proximally through the distal assembly and through the cannula portion, each leg terminating in a proximal end connected to the actuator. The actuator includes a trigger having first and second terminal positions defined by stops to limit motion of the trigger in each of first and second directions, respectively. Rotation of the trigger by a user simultaneously controls the position and tension of both cable legs to enable control of the articulation angle of the distal assembly by increasing tension on one of the first and second cable legs while not increasing tension on the other of the cable legs, such as by increasing tension on the first cable leg while simultaneously ensuring that no tension is placed on the second cable leg. In certain embodiments, the central portion of the cable is fixedly attached to the distal tip unit.

In some embodiments, the tissue manipulation includes blunt dissection and, in other embodiments, includes tissue manipulation utilizing a projecting feature such as a spatula tip or a duckbill tip. In yet other embodiments, tissue manipulation includes cold-cutting such as with shears or scissors having at least one movable cutting edge, or engaging tissue utilizing at least one moveable grasper-type jaw.

In certain embodiments, the distal tip includes at least one physical feature to assist aiming and/or orientation of the distal tip. The physical feature includes a geometric or topographical feature such as a ridge, a barrel or other sighting-type feature in some embodiments and, in a number of embodiments, includes at least one visually discernible marking, such as a laser-etched pattern.

In various embodiments, the instrument directs at least one type of surgical energy to a selected target site. In some embodiments, the surgical energy includes optical radiation delivered through at least one waveguide, which is hollow in certain embodiments.

This invention also features a surgical system including at least one energy source capable of producing at least a first surgical energy directable to a target location, and an articulating instrument for delivering the surgical energy to the target location.

BRIEF DESCRIPTION OF THE DRAWINGS

In what follows, preferred embodiments of the invention are explained in more detail with reference to the drawings, in which:

FIGS. 1A-1C are schematic side views of an instrument according to the present invention in straight, bent and intermediate positions, respectively;

FIGS. 2A and 2B are schematic side views of the distal assembly of the instrument of FIGS. 1A and 1B, respectively;

FIGS. 2C and 2D are enlarged views of the distal assembly of FIGS. 2A and 2B within circles C and D, respectively;

FIG. 2E is an enlarged view of the junction of two links within circle E of FIG. 2C;

FIG. 7 is a schematic perspective view of a distal tip segment according to the present invention;

FIG. 7A is a side view of the distal tip of FIG. 7;

FIG. 7B is a cross-sectional view along line B-B in FIG. 7A;

FIG. 7C is a front end view of the distal tip of FIG. 7;

FIG. 7D is a top view of the distal tip of FIG. 7;

FIG. 8 is a schematic perspective view of a link according to the present invention;

FIG. 8A is a side view of the link of FIG. 8;

FIG. 8B is a front end view of the link of FIG. 8;

FIG. 8C is a top view of the link of FIG. 8;

FIG. 8D is a cross-sectional view along line D-D in FIG. 8C;

FIG. 9 is a schematic perspective view of a union according to the present invention;

FIG. 9A is a side view of the union of FIG. 9;

FIG. 9B is a front end view of the union of FIG. 9;

FIG. 9C is a top view of the union of FIG. 9;

FIG. 9D is a cross-sectional view along line D-D in FIG. 9C;

FIG. 10 is a schematic top view of a distal assembly of the instrument of FIG. 1A showing inner and outer cannulas;

FIG. 10A is an enlarged view of the union and distal cannula portion of FIG. 10;

FIG. 10B is a cross-sectional view along line B-B of FIG. 10A;

FIG. 10C is a schematic side view of an alternative construction of the inner cannula of FIGS. 10-10B with at least one opening to assist sterilization between procedures;

FIG. 13 is a perspective view of another handpiece with trigger according to the present invention;

DETAILED DESCRIPTION OF THE PRESENTLY PREFERRED EMBODIMENTS

Figure 3:
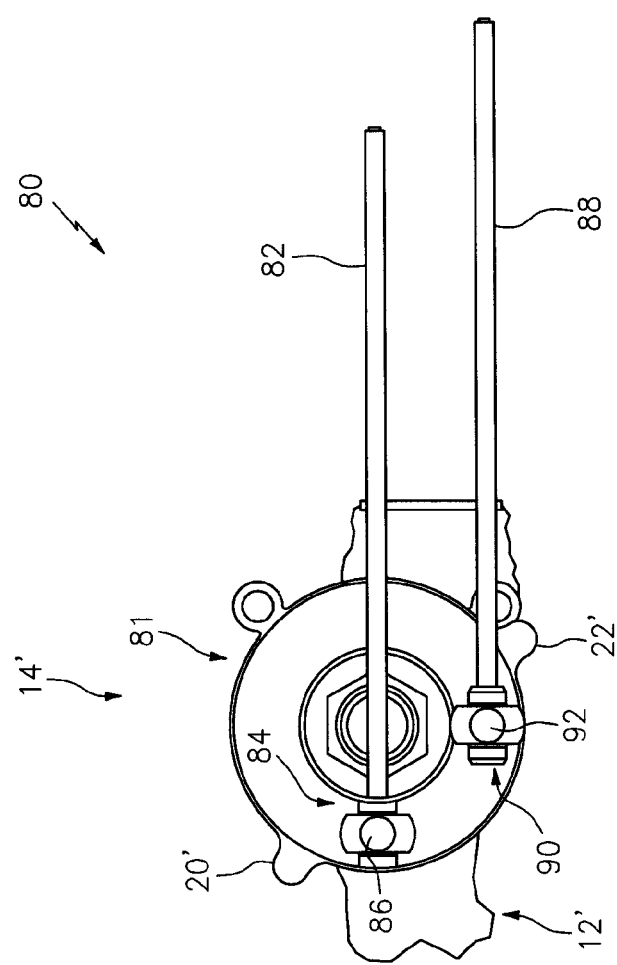
FIGS. 3 and 4 are schematic enlarged diagrams showing trigger and cable positions for the straight and bent positions of FIGS. 1A and 1B, respectively.

This invention may be accomplished by an articulating instrument having a distal assembly capable of moving among (1) a first configuration that is substantially straight or at a first curved orientation, (2) a second configuration at a second curved orientation, and (3) a plurality of intermediate configurations between the first and second configurations. One or both of the first and second configurations are substantially stable such that the distal assembly of the instrument has a tendency to remain in whichever of the first and second configurations it is placed by a user of the instrument. Preferably, the distal assembly defines at least one distal feature, such as a flattened, "forked" or bifurcated tip, that is useful for manipulating tissue.

Handpiece 10 according to one construction of the present invention, FIGS. 1A-1C, is a surgical instrument having a handle 12, a trigger or actuator mechanism 14, a cannula portion 16, and a distal assembly 18 that is movable among straight, fully bent or curved, and variable intermediate positions, also referred to as configurations or orientations, as illustrated respectively in FIGS. 1A-1C. Trigger 14 has an upper projection 20 and a lower projection 22 in this construction that can be actuated by a user's thumb and forefinger, for example. Upper and lower projections 20, 22 are also referred to as levers or buttons, and trigger 14 is also referred to as a switch or actuator. Upper projection 20 is moved fully downwardly, which rotates trigger 14 in a first, counter-clockwise direction as viewed in FIG. 1A, to achieve a straight configuration that is typically preferred for insertion of the distal assembly 18 into a patient. Lower projection 22 is moved fully upwardly, which rotates trigger 14 in a second, clockwise direction as viewed in FIG. 1B, to achieve the fully bent or curved configuration. Projections 20 and 22 are approximately equally spaced from handle 12 in the middle of the variable intermediate configuration, shown as "slightly" or "partially" bent or curved in FIG. 1C. In other words, in this construction the curvature of the distal assembly 18 can be varied continuously by a user between the terminal or extreme first and second configurations.

Cannula portion 16 and distal portion 18, also referred to as distal assembly 18, are shown in more detail in FIGS. 2A and 2B in the straight and fully bent positions, respectively. Distal portion 18 includes a distal tip unit or segment 30, an articulating links section 32, and a union 34 which is rigidly connected to cannula portion 16 as described in more detail below; outer cannula 50 is visible in FIGS. 2A-2D. In one construction, outer cannula 50 and distal portion 18 have an overall combined length $L_1$ of approximately 33 cm (13 inches) in the straight position illustrated in FIG. 2A, and distal portion 18 has an overall length $L_2$ of approximately 4.8 cm (1.9 inches) as shown in FIG. 2C.

Articulating links section 32 is comprised of four link units 40, 42, 44 and 46 in this construction. Relative to the longitudinal axis 52 of cannula portion 16, FIG. 2D, arrow 54 indicates negative articulation and arrow 56 represents positive articulation along a plane of articulation. As illustrated in FIG. 2D, distal tip 30 is at a maximum articulation angle $A_M$ of approximately 60 degrees to 65 degrees in this construction when fully articulated, with a minimum of 58 degrees and a maximum of 70 degrees. The maximum articulation angle $A_U$ of each unit about its pivot pin is approximately 11 degrees to 14 degrees, as indicated between line 58, representing the longitudinal axis of link 40, and line 60, representing the longitudinal axis of distal tip 30. As explained in more detail below, slight negative articulation may be desired in certain circumstances to enhance positive locking stability in the "straight" configuration; typically, the articulation is "one-sided", that is, articulation is primarily in the positive direction of arrow 56. In other constructions, the first configuration is negatively curved rather than "straight", and the links are more symmetrical rather than asymmetrical as shown in FIG. 2E.

The total articulation angle is a function of link-to-link articulation angle and total number of links in the design. Also, the bend radius is a function of the link-to-link articulation angle $A_U$ and length of each link. It is desirable to construct the bend radius such that the bend losses in the waveguide are minimized by controlling the maximum bend radius permissible in the articulating portion of the handpiece. In one construction, the total distance travelled by distal tip 30 is approximately 3 cm between the first and second terminal configurations.

As shown in more detail in FIG. 2E for the junction of links 44 and 46, a distal-facing, asymmetric shoulder 62 is formed on link 46 that engages a proximal projection or finger 64 of link 44; a matching finger 66 extends proximally over a pivot surface on the opposite side of link 46 and is not visible in FIG. 2E. In other words, fingers 64 and 66 extend substantially parallel to the plane of rotation, also referred to as the bend plane, that is indicated by arrows 54 and 56 in FIG. 2D, and slide over pivot surfaces of link 46 as described in more detail below. One side of the distal shoulder 62, FIG. 2E, has a flat stop or land 72 that engages one side of proximal finger 64 of link 44 while the other, articulating side of shoulder 62 has a curved slope 74 to permit additional movement of proximal finger 64 about pivot pin 48 and thereby allow articulation of link 44 up to angle $A_U$, FIG. 2D.

Figure 4:
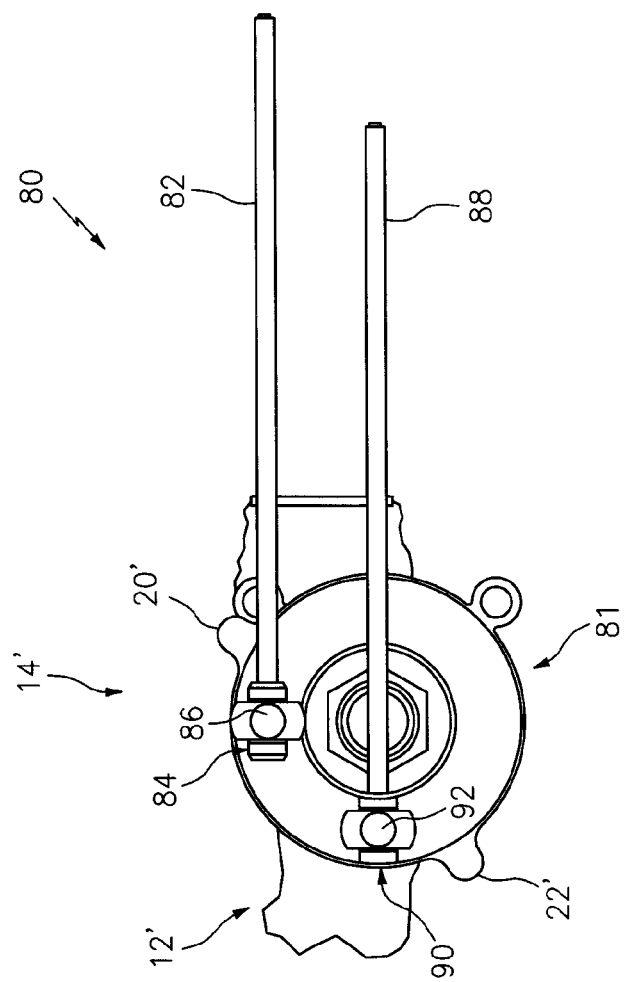

A proximal portion 80 of the trigger and cable system which accomplishes articulation between the straight and bent configurations, each preferably being a stable position, is illustrated in enlarged, schematic detail in FIGS. 3 and 4, respectively, for a trigger 14' with articulation wheel 81 carried by a handle 12'. A first cable 82 has a proximal end 84 fixedly held by a fastener 86 and a second cable 88 has a proximal end 90 fixedly held by a fastener 92. Fasteners 86 and 92 are mounted on rotatable trigger 14' which has outer projections 20' and 22' that are manipulated by a user to change the curvature of the distal portion of the instrument between the two stable positions shown in FIGS. 1A-1B and 2C-2D. In other constructions, the articulation wheel is asymmetrical and/or cable ends 84 and 90 are arranged asymmetrically relative to each other. In yet other constructions, a rack and pinion-type mechanism is utilized instead of a rotating wheel.

Once placed into one of those stable positions, deliberate force must be applied to trigger 14' to move out of the stable position. For the straight configuration, FIG. 3, first cable 82 is in tension and locked because it has pulled links 32 together about the hinge pins; each hinge pin can be considered a fulcrum as well as a pivot point. Referring to FIG. 2E, link 44 is pulled by first cable 82 about pin 48 and finger 64 is driven against hard stop or land 72 in the straight configuration shown in FIG. 2C. Simultaneously, second cable 88 is relaxed and unlocked.

Figure 5:
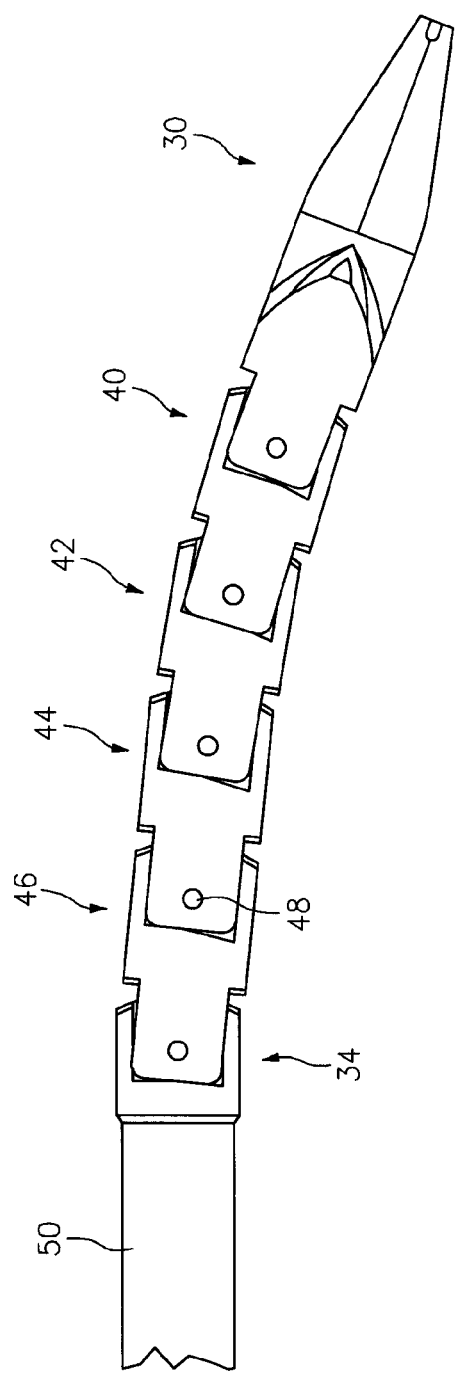
FIG. 5 is an enlarged schematic view of the distal assembly of FIG. 1C in the intermediate position.
Figure 6:
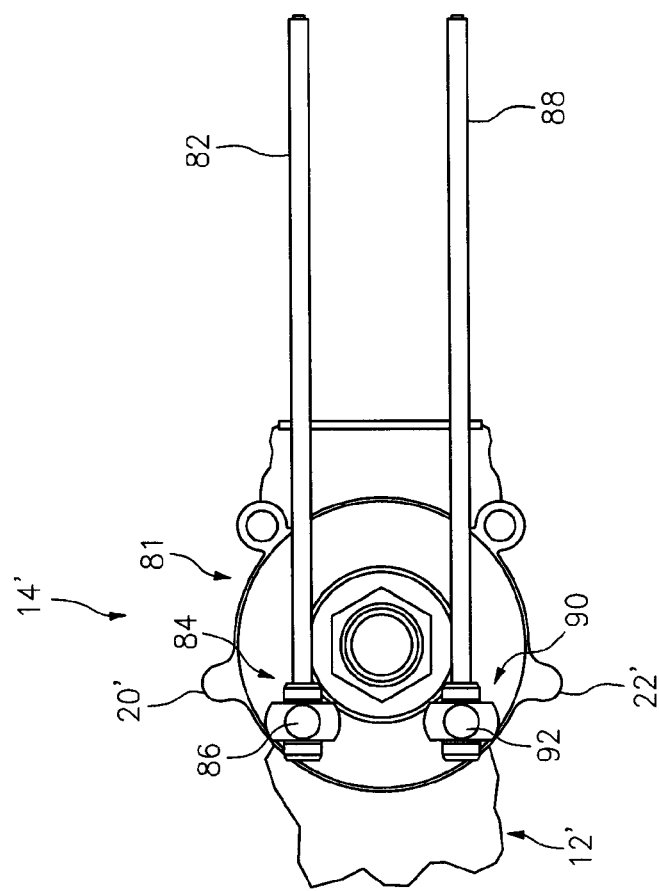
FIG. 6 is a schematic enlarged diagram showing trigger and cable positions for the intermediate position of FIGS. 1C and 5.

For the fully curved or bent configuration, FIG. 4, the first cable 82 is relaxed and the second cable 88 is in tension and locked because cable 88 has pulled the links together about the fulcra in the positive articulation direction shown by arrow 56 in FIG. 2D. By comparison, the continuously-variable intermediate configurations, for which one "middle" position is shown in FIG. 1C and FIGS. 5-6, are neutrally stable and unlocked, with neither cable 82 nor cable 88 in tension; manual force must be continually applied to resist changes in curvature if the distal tip is brought into contact with tissue or other objects while the instrument is in one of the intermediate configurations.

Once the distal portion 18 is "locked" in the straight configuration or in the fully curved configuration, tissue can be manipulated and/or treated as desired, in part according to the type of distal tip that has been selected by a surgeon for a particular procedure, without manually applying force to the trigger to maintain its rotational position relative to the handle. One benefit of the present invention is that no additional locking mechanism is needed; instead, the locking/unlocking and amount of articulation are controlled smoothly and continuously by rotation of the single trigger or actuator using one or two fingers, without any additional action by the user. The "duckbill" design for distal tip 30, as shown in more detail in FIGS. 7-7D, is flattened along one plane to form at least one face 100, 102 and is rounded along another, preferably perpendicular plane to form rounded edges 104, 106 in this construction. This flattened design readily enables surgeons to use the face to accomplish blunt dissection and other types of tissue manipulation. Physical features assisting beam aiming are described below.

As also described in more detail below, the duckbill design has a symmetry about the laser energy beam emitted from a waveguide carried by the handpiece. In other words, the duckbill tip has the same appearance whether viewed from above or below. By comparison, a spatula-type tip is asymmetric; several variations of asymmetric distal tips are shown in FIG. 3 of U.S. Patent Publication No. 2014/0088577 by Anastassiou et al. and a standoff tip that is offset to one side of a laser beam axis is shown in FIG. 1 of U.S. Pat. No. 7,167,622 by Temelkuran et al., for example. Further, the faces of the duckbill can be oriented relative to the bend plane of the distal portion, such as being aligned (i) with the bend plane or (ii) perpendicular to the bend plane. In this construction, the bend plane is also the stiffest plane when the instrument is in one of the "locked" configurations as described above.

Distal tip 30 defines proximally-extending fingers 110 and 112, each of which defines a hole 114, 116, respectively, through which a pivot pin is placed to secure tip 30 to a link. Tip 30 further defines an inner cavity 118 that is widest proximally and tapers distally, terminating in a reduced-diameter stop which limits further insertion of a waveguide. A distal opening 120, FIG. 7B-7C, allows laser radiation to be emitted. Openings 122, 124 enhance cleaning and sterilization of distal tip 30 between procedures and also enhance visual ascertainment that a waveguide has been fully inserted within the handpiece.

Preferably, the tip 30 further includes a diverging, bifurcated fork-type structure 126 with a narrow opening 120 near the distal outlet of the waveguide, with a progressively wider channel 128 extending distally. More preferably, the progressive distal divergence of the channel 128 is substantially the same as the divergence of the laser beam, as described in more detail below, to provide a visual indication of where an energy beam will be directed once the instrument is energized, such as by directing optical radiation through a waveguide within the handpiece. This correspondence between channel divergence and energy beam divergence assists aiming and positioning of a non-visible laser beam relative to target tissue. Preferably, the structure 126 does not interfere or "clip" an energy beam directed through opening 120.

Moreover, the fork 126 serves as a physical guide for cutting tissue when the tissue to be cut or removed is placed within channel 128. For example, tissue adhesion to be severed can be placed within the channel 128 of fork 126, before or during energizing the instrument, to positively and accurately lyse the adhesion across its thickness. This is particularly effective while moving fork 126 along the mass of the adhesion, in a manner similar to shears severing a cloth.

Distal tip 30 further defines a channel 130 within the main body of tip 30 through which an articulation cable is passed during assembly of an instrument according to the present invention. In one construction, the midpoint of a length of cable is marked, and the two ends of the cable are threaded proximally into the tip body to emerge proximally through passages 132 and 134. The ends of the cable are then threaded through the links, the union, and then between the inner and outer cannulas as described below. For some constructions, the midpoint of the cable then is secured to the tip 30 within channel 130 by brazing, welding or other fastening technique, depending on the composition of the cable and the distal tip 30. In this manner, a single length of cable functions mechanically as first and second cables during articulation as described above.

In other constructions, the midpoint of the single cable is not bonded to the distal tip unit to enable slippage of the cable relative to the distal tip unit if excessive force is applied by the user, such as during tissue manipulation. Depending on the dimensions and coefficients of friction of the cable and the channel or other passage in the distal tip unit through which the cable passes, a threshold for externally applied force is established, beyond which the cable will slip by overcoming frictional resistance within the distal tip unit. Such slippage enables the cable to adjust its length in the two sections to automatically regulate tension in the cable to minimize breakage of the cable during extreme use. Alternately, two separate cables can be used which will then both need to be fastened to, or otherwise associated with, the distal tip.

Preferably, the overall external contours of distal tip 30 are relatively streamlined to enhance insertion through natural body orifices, incisions or trocar seals, according to surgeon preference. The largest cross-sectional geometry is generally circular in this construction.

Each link, such as link 46 shown in more detail in FIGS. 8-8D, preferably has at least one hard stop feature to limit articulation and enhance rigidity of the instrument during tissue manipulation. In some constructions, an asymmetric link design enhances articulation along a single plane of movement. Planar pivot surfaces on adjacent "mating" links minimize lateral movement of the entire assembly.

Link 46 has proximally-extending fingers 140, 142 which define holes 144, 146, respectively, through which pivot pins are placed to secure it to the pivot surfaces of a more proximal link or, in this construction, to union 34 as described in more detail below. A distal portion of link 46 defines flat pivot surfaces 148, 150, each of which is substantially parallel to the plane of articulation and defines a pivot hole, such as hole 152 in pivot surface 148, to pivotally secure a finger from a distal link or, for the distal-most link, from a distal tip.

As described above in relation to FIG. 2E, pivot surface 148 terminates proximally at a distal-facing shoulder 62 which has a flat stop or land 72 that engages one side of proximal finger 64 of link 44 while the other, articulating side of shoulder 62 has a curved slope 74 to permit additional movement of proximal finger 64 about pivot pin 48 and thereby allow articulation of link 44.

Each link and union preferably defines a central lumen to removably house a waveguide inserted therethrough. Link 46 defines central lumen 160, FIGS. 8B-8D. In preferred constructions, a waveguide is initially inserted through the proximal end of the handle and each link unit defines its central lumen with distally-tapered walls to aid insertion of each single-use waveguide so it is "centered" before passing to the next link. The taper minimizes risk of the waveguide catching on an edge of the lumen while the waveguide is being inserted. Link 46 also defines passages 162 and 164 through which ends of the articulation cable are inserted.

Union 34, shown in more detail in FIGS. 9-10B, is a non-articulating member of the distal assembly 18 enabling the distal ends of elongated inner cannula 51 and outer cannula 50, FIGS. 10-10B, to be welded at the proximal region of union 34. An articulating link, such as link 46, is pivotally attached at a distal region of the union 34, preferably by at least one hinge pin. Features which are similar to link 46 are indicated by corresponding reference numbers followed by a prime designation. For example, union 34 defines pivot surfaces 148' and 150' and a central lumen 160'. Similarly, the union 34 includes a land 72', a curved slope 74', a hole 152', and passages 162' and 164', which are substantially the same as the land 72, curved slope 74', hole 152, and passages 162 and 164 as described previously herein, for example, with respect to the link 46. Instead of proximally-extending pivot fingers, however, union 34 has inserts 170 and 172 which are slid between inner and outer cannulae 51 and 50 during assembly of the instrument.

Outer cannula 50 provides a protective housing for the articulation cables, which are inserted through a passage 196, which is toroidal in cross-section in this construction as defined by the outer and inner cannulae 50 and 51. Preferably, outer cannula 50 is substantially rigid and adds to the structural integrity of the instrument.

Inner cannula 51 provides a continuous unobstructed path via inner lumen 198 to facilitate waveguide insertion and may also be substantially rigid. Moreover, inner cannula 51 maintains a physical separation between the waveguide and the movable articulation cables. As illustrated in FIG. 10C for an alternative inner cannula 51', in some constructions at least one opening 197, such as a circular hole or a non-circular slot, is provided to enhance fluid communication between one or more lumens defined by the inner cannula 51' and the toroidal passage between cannula 51' and an outer cannula. In one sterilization technique, sterilizing and/or flushing fluid is introduced from the distal end of the instrument to flush internal spaces proximally. The sterilizing fluid enters the space between the cannulae through the one or more openings 197 and then exits proximally through the handle. In one construction, four openings 197 are 0.016 inch (0.41 mm) in diameter holes spaced 90 degrees apart about the circumference of cannula 51'. As indicated by arrow 195, each hole 197 is spaced approximately 0.25 inch (6.4 mm) from distal end 199 in that construction.

Inner cannula 51 is longer than outer cannula 50 in this construction. The proximal ends of the inner and outer cannulae 51 and 50 are attached to the handle as described below.

Figure 11:
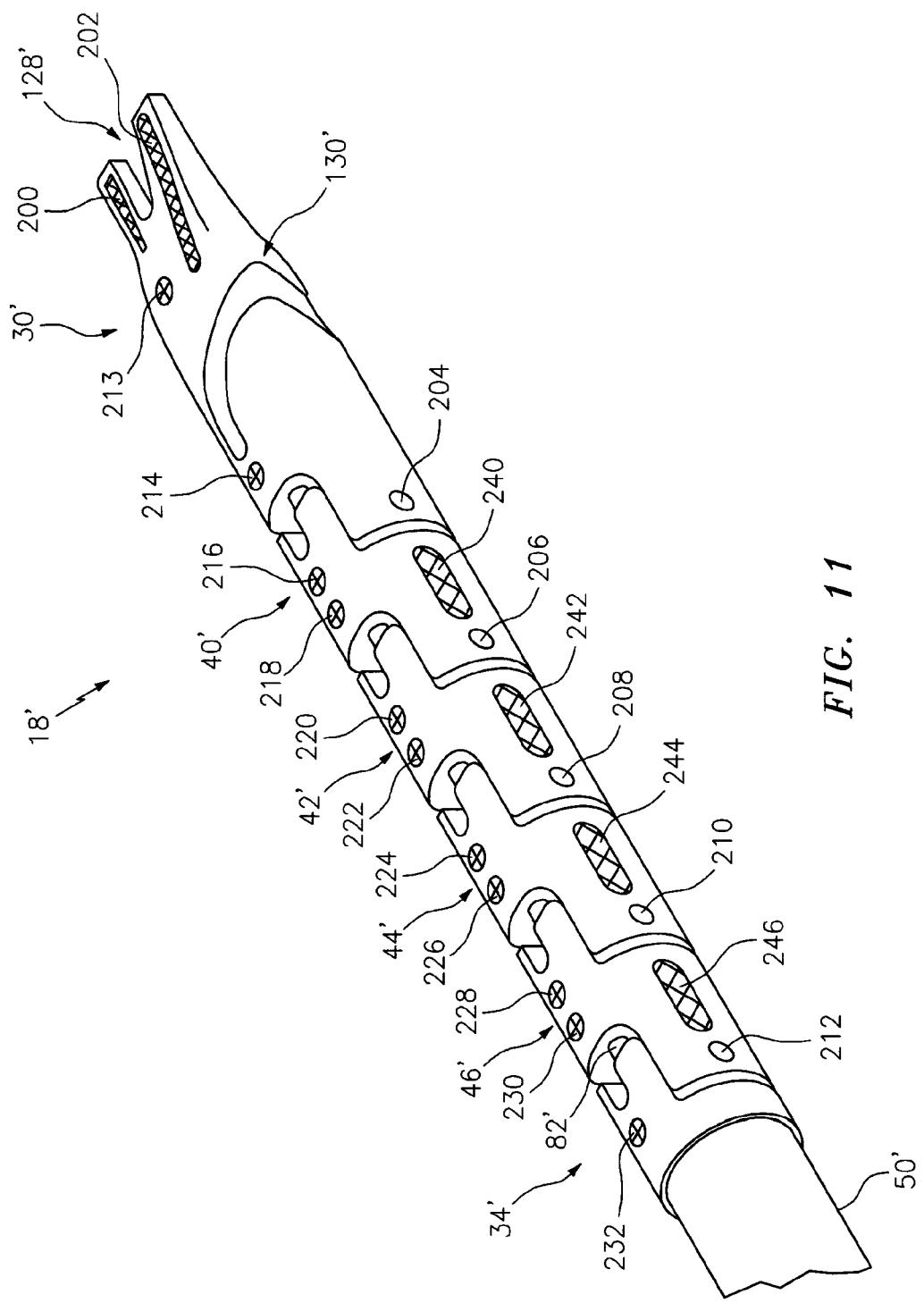
FIG. 11 is an enlarged schematic perspective view of a distal assembly according to the present invention with various indications placed thereon.

In one construction of a distal portion 18', FIG. 11, a distal tip 30' has laser-etched, visually discernible markings 200, 202 on either side of fork channel 128' to enhance aiming. Distal tip 30' defines cable slot 130' and is pivotally secured to link 40' by a hinge pin 204 on one side and by a similar pin (not visible) on the other side. In a similar manner, links 40', 42', 44', and 46' are secured to each other and to union 34' by pins 206, 208, 210 and 212, respectively. Portions of cable 82' are visible between the links 40'-46', the union 34' and the distal tip 30'.

Marker dots 213 and 214 are provided on distal tip 30' and pairs of marker dots 216-218, 220-222, 224-226, and 228-230 are provided on links 40', 42', 44' and 46', respectively. A marker dot 232 is provided on union 34' in alignment with the other marker dots, all of which preferably lie along the bend plane. Spacing between the marker dots will change as the distal portion 18' is articulated. Elongated markings 240, 242, 244 and 246 on links 40', 42', 44' and 46', respectively, lie along a plane orthogonal to the bend plane and help to differentiate the orientation and articulation of the distal portion 18'. In some constructions the markings include one or more contrasting colors and, in other constructions, the markings include radiopaque material.

Figure 11A:
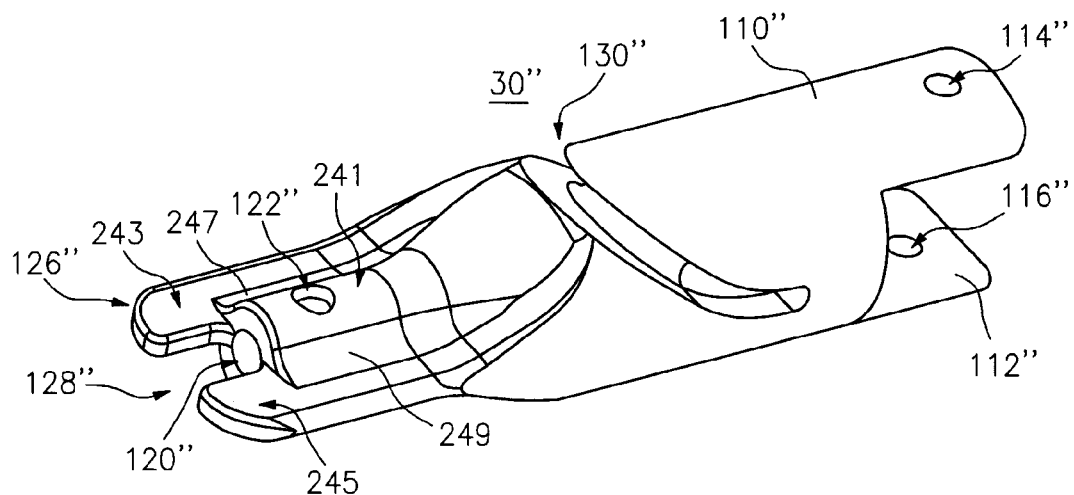
FIGS. 11A and 11B are schematic front and rear perspective views of an alternative distal tip according to the present invention.
Figure 11B:
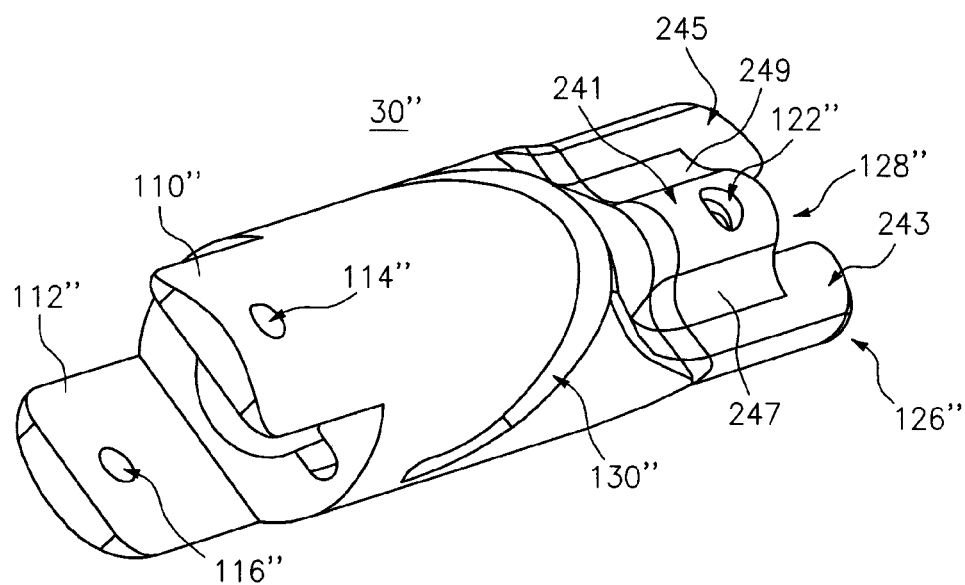

Instead of, or in combination with, the aiming markings 200 and 202, FIG. 11, a distal tip 30", FIGS. 11A-B, defines an axially-extending, barrel-type guide 241 which serves as a physical indicator for aiming as it shows the location of the waveguide within the distal tip 30". Other features similar to distal tip 30, FIGS. 7-7D, are indicated by similar reference numbers with double-prime marks in FIGS. 11A-B. For example, fork-type structure 126" includes projections 243 and 245 which define a channel 128" between them. Similarly, the distal tip 30" includes proximally-extending fingers 110" and 112", holes 114" and 116", a distal opening 120", and a channel 130" within the main body of the distal tip 30". Structure 126" is oriented at a 90-degree rotational offset relative to structure 126, FIGS. 7-7D. Ramps 247 and 249, FIGS. 11A-B, provide a contoured transition between the relatively flat surfaces of projections 243 and 245 and the cylindrical shape of guide 241.

Figure 12A:
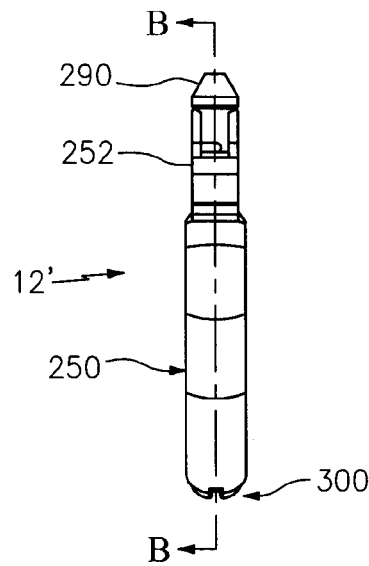
FIG. 12A is a top view of the handle in FIG. 12.
Figure 12B:
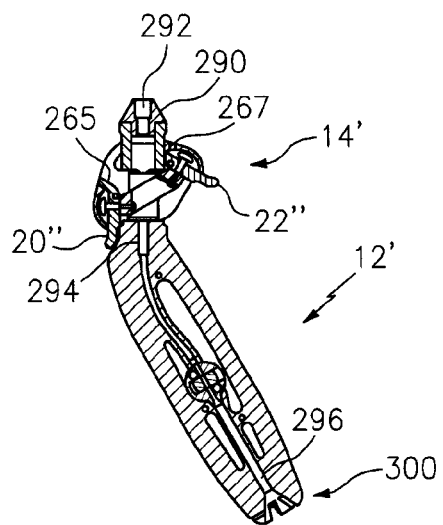
FIG. 12B is a cross-sectional view along line B-B in FIG. 12A.
Figure 12:
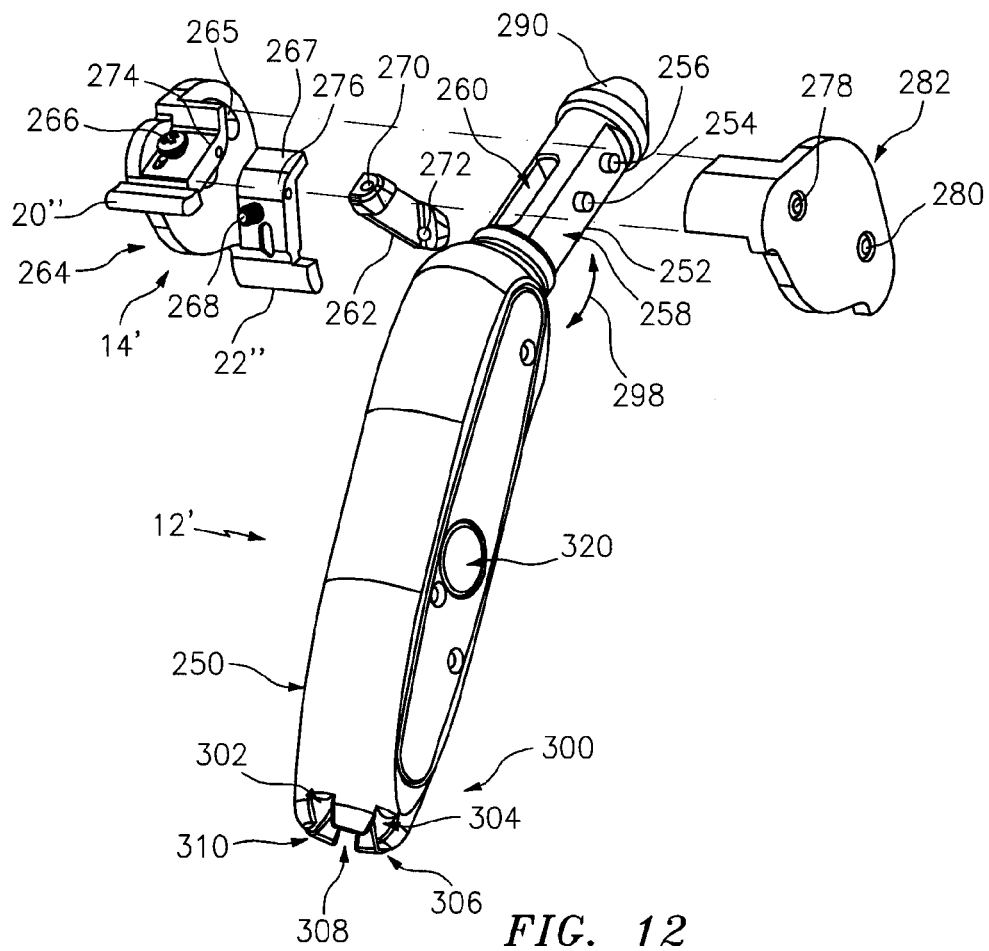
FIG. 12 is a schematic, partially-exploded view of a handle and trigger according to the present invention.

A handle 12', FIGS. 12-12B, has a main body covered with a hand grip 250 and has a distally-extending trigger support 252 with cylindrical projections 254 and 256 extending transversely from flat surface 258; a similar flat surface and matching dual projections are defined on the opposite side (not shown) of trigger support 252. Projection 254 serves as a pivot point for trigger 14' while projection 256 serves as a stop to limit trigger rotation when contacted by trigger stop surfaces 265 or 267 of projection pieces 20" or 22", respectively. As discussed above, the rigidity of distal tip 18 may be enhanced if hard-stops on the links engage prior to engagement of the trigger stops, which increases inherent stability for those configurations. Trigger support 252 further defines an opening 260 which receives cable lock piece 262 of trigger 14'. In this construction, trigger 14' further includes a switch 264 with projection pieces 20" and 22" and fasteners 266, 268 which engage holes 270, 272 defined in cable lock piece 262. Projection pieces 20" and 22" further define holes 274, 276 which receive fasteners 278, 280 of a switch cover or cap 282.

Trigger 14' is shown assembled in cross-sectional view in FIG. 12B. Cable lock piece 262 secures the proximal ends of first and second cables (not shown) such as illustrated for cables 82 and 88 in FIGS. 3, 4 and 6 above. In one construction, the ends of each cable are tensioned and then locked by screws carried by cable lock piece 262 or to the switch 264. Preferably, the ends are then welded to the cable lock piece 262 to ensure fixation.

A nose cap 290 defines a first passage 292 that receives the proximal end of outer cannula 50, FIG. 10. In one construction, the proximal end of cannula 50 is welded to nose cap 290 which, in turn, is welded to trigger support 252. A narrower passage 294 receives the proximal portion of inner cannula 51. The body of handle 12' further defines a still-narrower passage 296, FIG. 12B, through which a single-use waveguide is inserted prior to use of the instrument in a surgical procedure. At least one single-use waveguide passes through the handpiece 12' such as described in general by Temelkuran et al. in U.S. Pat. No. 7,331,954. In some constructions, the inner channel 296 is machined or otherwise formed into the body of the handle to carry the waveguide and thereby eliminate the need for a separate, internal cannula to hold the waveguide within the handle before the waveguide reaches the proximal end of inner cannula 51.

Double-ended arrow 298 indicates an alternative embodiment in which support 252 is rotatably coupled to the body of handle 12' to enable rotation about the longitudinal axis of cannula portion 16. This rotational coupling, preferably enabling about 360 degrees rotation, provides another degree of freedom of movement of a distal tip 18, in addition to selective articulation as driven by rotation of trigger 14' within a plane containing the longitudinal axis of cannula portion 16. A user can thereby achieve 360 degrees of access within a patient without altering his or her grip on the handpiece. This configuration also ensures that the articulating mechanism of trigger 14' remains coplanar with the bend plane of distal portion 18, so the user intuitively knows which way the bend plane is oriented within a patient. A ball-and-spring detent with corresponding recess, or similar catch with release mechanism or a lock, may be provided to encourage stability in certain positions of trigger 14' and/or support 252 when it is rotatable.

The grip 250 preferably is curved to provide enhanced ergonomic grip and to ensure that no portion of the waveguide held by the handpiece is "aimed" at a user's body as the waveguide exits the handpiece proximally. Additional protection against inadvertent leakage into a user, especially if the user rests handle 12' against the user's body, of laser radiation or other surgical energy passing through a waveguide is provided by guard 300 which defines a plurality of grooves 302, 304, 306, 308 and 310 in this construction, similar to "crenellations" of a "rook" or "castle" chess piece; one or more of the projecting "crenellations" will rest against the user's body and serve as stand-offs while an exposed portion of the waveguide is pressed into one of the grooves 302-310. In other words, when the user's body forces a small radius bend in an exposed portion of the waveguide, that portion can bend without kinking because it becomes protected within one of the grooves 302-310 and avoids further bending forces.

Handle 12' further carries a waveguide lock mechanism 320. Several mechanisms for locking the waveguide within the handpiece, also referred to as fiber locks, as well as counterbalance adjustments for handpieces, are disclosed by Shurgalin et al. in U.S. Patent Publication No. 2014/0316395, also published as WO2014/143688, assigned to OmniGuide, Inc.

Figures 13A, 13B:
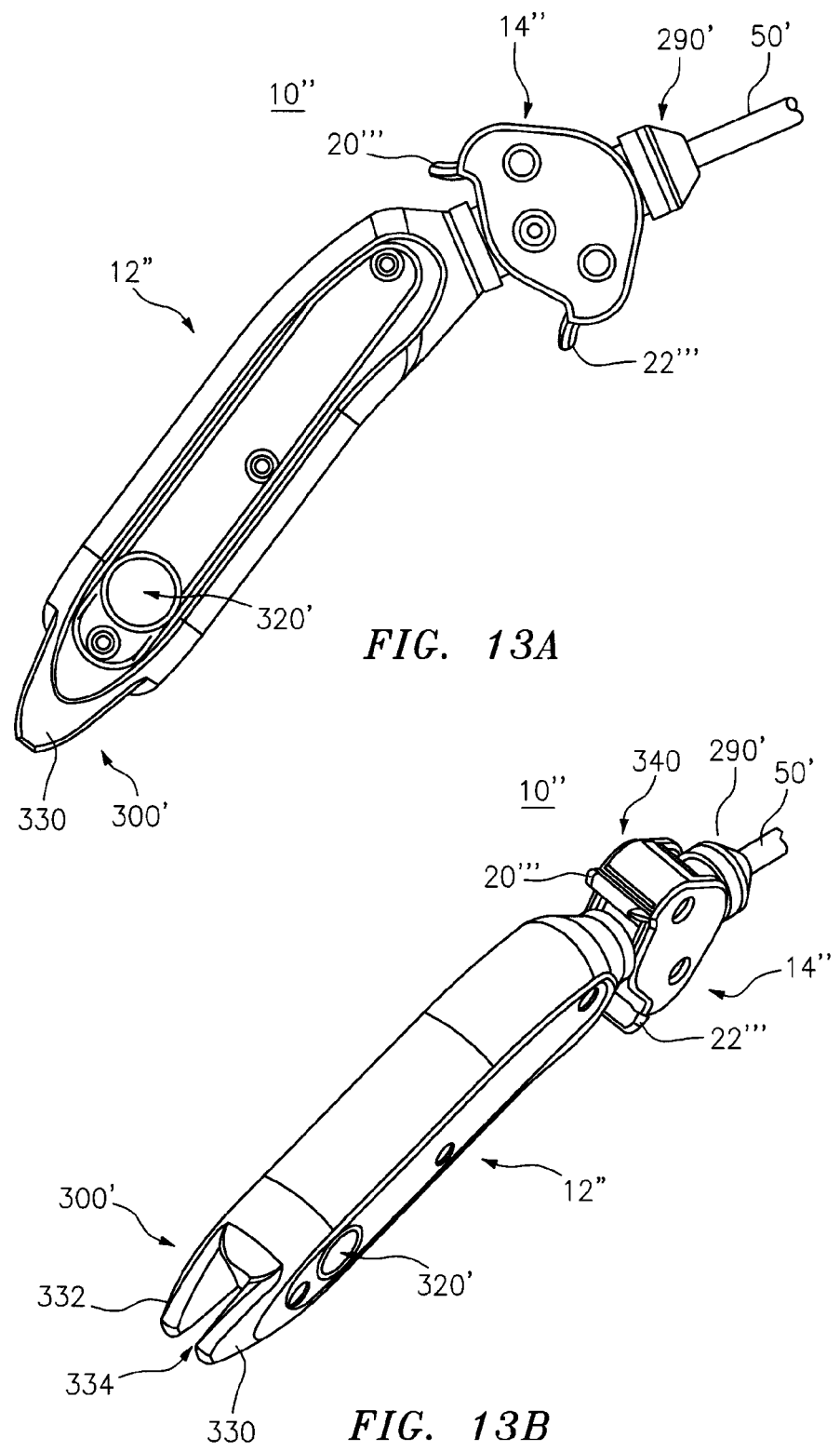
FIG. 13A is a side view of the handpiece and trigger of FIG. 13.

An alternative configuration for proximal components of an instrument 10" according the present invention is shown in FIGS. 13-13A for a handle 12", a trigger actuator mechanism 14", a nose cap 290' and an outer cannula 50'. Trigger actuator 14" has a textured or higher-friction surface, such as provided by actuator grooves 340 located near projections 20''' and 22''', to enhance tactile feedback for actuator position.

Handle 12" has a waveguide lock 320' and a waveguide guard 300'. The guard 300' has rounded elongated projections 330 and 332 extending proximally and defining between them a cavity 334 into which an exposed portion of a waveguide is guided to bend, along a single plane only, when that portion of the waveguide presses against a user. Excessive bending increases energy losses within the waveguide and may cause the waveguide to fail. In other constructions, the waveguide is placed through a flexible polymeric sleeve, have a stiffer distal portion attached to a proximal portion of the handle, to minimize bending for the otherwise exposed portion of the waveguide.

Instruments according to the present invention can be inserted through access devices such as trocars. A trocar typically includes a cannula, with a proximal seal housing, that is temporarily placed through an incision in the skin and underlying muscle; one or more instruments are passed through the trocar to conduct minimally invasive surgery within a body cavity. In other procedures, one or more natural body orifices are utilized. Other tools, such as retractors, suction, irrigation, or tissue manipulation or removal devices may be introduced through the same or other incisions or orifices by humans or by robotic surgical systems.

Examples of known robotic surgical systems utilizing lasers and other instruments are provided by Mohr in U.S. Patent Publication No. 2009/0171372, by Williams et al. in U.S. Patent Publication No. 2009/0248041 and by Prisco et al. in U.S. Patent Publication No. 2010/0249507, for example, all assigned to Intuitive Surgical Operations, Inc. and/or Intuitive Surgical, Inc. of Sunnyvale, Calif., which provides the DA VINCI robotic platform. Robotically assisted surgery through a single port utilizing an image capturing device and multiple surgical tools is described by Mohr in U.S. Pat. No. 8,517,933.

System control settings for a surgical energy device typically include power settings such as at least one of power level, pulse rate, pulse width, pulse shape and duty cycle for delivery of electromagnetic radiation by the surgical energy device. In certain constructions, at least one fluid source delivers at least one gas or liquid to a target location.

In some constructions, the source of optical radiation is part of a laser surgery system such as the INTELLIGUIDE Laser System commercially available from OmniGuide, Inc. of Cambridge, Mass. The laser surgery system typically includes a human interface, including buttons, dials, knobs or a touch screen, which can be used to select the laser power settings in some constructions. Systems optionally includes at least one fluid source, which generates a first fluid flow and is part of the laser surgical system in some constructions. At least one fluid flow valve, actuated via a control such as a footswitch, and a chiller/heater are provided for the fluid source in some constructions. It may also optionally include a second fluid source with its own independent fluid flow valve and chiller/heater. In other constructions, knobs, buttons or touch screen control replaces one or more foot controls. When the energy source includes a laser and is part of a laser surgery system, the laser surgery system may also includes a flexible waveguide for delivering laser radiation to the surgical site such as the BEAMPATH flexible fiber waveguides available from OmniGuide, Inc. The waveguide is hollow in some constructions. An articulated arm may also be used to deliver free space laser beams to the surgical site. One source of fluid may directed to the center of the hollow waveguide and a second source to an annular area surrounding the waveguide, such as described in more detail by Fuflyigin et al. in U.S. Provisional Application No. 61/929,343 filed 20 Jan. 2014.

Another approach is to make the energy spot size smaller by focusing optical energy using lenses or by controlling the distance between tissue and the energy exit point, such as when an optical fiber is used to guide energy to the tissue. Certain techniques of altering the energy spot size utilizing optical components in a handpiece are provided by Shurgalin et al. in U.S. Patent Publication No. 2013/0064515.

Yet another approach is to direct cooling fluid preferentially around the spot relative to its center, as further described by Fuflyigin et al. in U.S. Provisional Application No. 61/929,343.

The relationship between tissue temperature and tissue change, for both tissue effect and visual effect, is shown in Table I:

TABLE I

| TEMPERATURE | TISSUE EFFECT | VISUAL EFFECT |
| --- | --- | --- |
| 37° C.-60° C. | Heating | No Change |
| 60° C.-90° C. | Denaturation/ Onset of Coagulation | White/Grey |
| 90° C.-100° C. | Drying/Puckering | Wrinkling/ Puckering |
| 100°+ C. | Vaporization (Cutting/Ablation) | Golden/Char/Smoke |

When water in tissue reaches 100° C., water vapor and solid particulates are created, which appears as "smoke". Whether cutting or ablation occurs depends on several system control settings as described in more detail below.

Laser surgery typically utilizes long, thin, flexible solid or hollow waveguides to deliver specific wavelengths of electromagnetic radiation. Solid core silica fibers, for example, are utilized to guide wavelength of KPT (532 nm), Nd:YAG (1.06 µm), Ho:YAG (2.1 µm) and Tm:YAG (2 µm) lasers for various medical applications. For $CO_2$ laser beams (approximately 10.6 µm wavelength), hollow waveguides are useful, as the $CO_2$ wavelength is generally highly absorbed in materials traditionally used for optical fibers, such as silicates and thermoplastic polymers. A high omnidirectional reflector is disclosed in U.S. Pat. No. 6,130,780 to Joannopoulos et al.

Flexible hollow waveguides are manufactured in some techniques by drawing structured thermoplastic preforms. Examples of such a structure are described by Harrington et al. in U.S. Pat. No. 5,440,664 and by Fink et al. in U.S. Pat. Nos. 6,463,200 and 7,311,962, in which a dielectric stack of materials having different refractive indices is arranged in concentric cylinders about the waveguide axis thus providing the mirror structure that guides the radiation. Flexible hollow waveguides drawn from structured thermoplastic preforms are also disclosed in U.S. Pat. No. 7,272,285 to Benoit et al. and U.S. Pat. No. 7,295,734 to Bayindir et al., as well as in the following U.S. Patents assigned to OmniGuide, Inc.: U.S. Pat. No. 6,788,864 by Ahmad et al.; U.S. Pat. No. 6,801,698 by King et al.; U.S. Pat. No. 6,898,359 by Soljacic et al.; and U.S. Pat. No. 7,142,756 by Anderson et al.

At times, certain surgical uses of energy delivery devices such as waveguides may result in tissue debris, fluid, or smoke being generated. Such tissue debris may absorb delivered energy, including backscattered laser energy, and heat or otherwise interfere with the waveguide. Such tissue debris may impede or slow normal passive cooling resulting from thermal dissipation, and/or impede more active cooling resulting from delivered fluid, including gas flow through the waveguide core. The combination of increased heating and reduced cooling may overheat and thus damage the waveguide.

One approach to protect the portion of the surgical energy device is to flow fluid through a conduit such as hollow core waveguides. Gas flow may be used for clearing tissue debris and blood during tissue cutting, for cooling the waveguide and for therapeutic reasons such as assisting tissue coagulation. The gas flowing out of the waveguide may also assist in keeping the waveguide core from clogging and from damage due to the splattering, splashing, or deposition of tissue debris, including smoke and fluids. Protection of the waveguide distal end may also be achieved by a tip attached to the waveguide distal end, such as disclosed by Temelkuran et al. in U.S. Pat. Nos. 7,167,622 and 7,331,954, by Goell et al. in U.S. Pat. No. 8,280,212, and by Anastassiou et al. in U.S. Patent Publication No. 2014/0088577, all assigned to OmniGuide, Inc. of Cambridge, Mass. A solid distal optical tip which may have one or more cutting edges is described in U.S. Pat. No. 5,951,543 by Brauer.

Figure 14A:
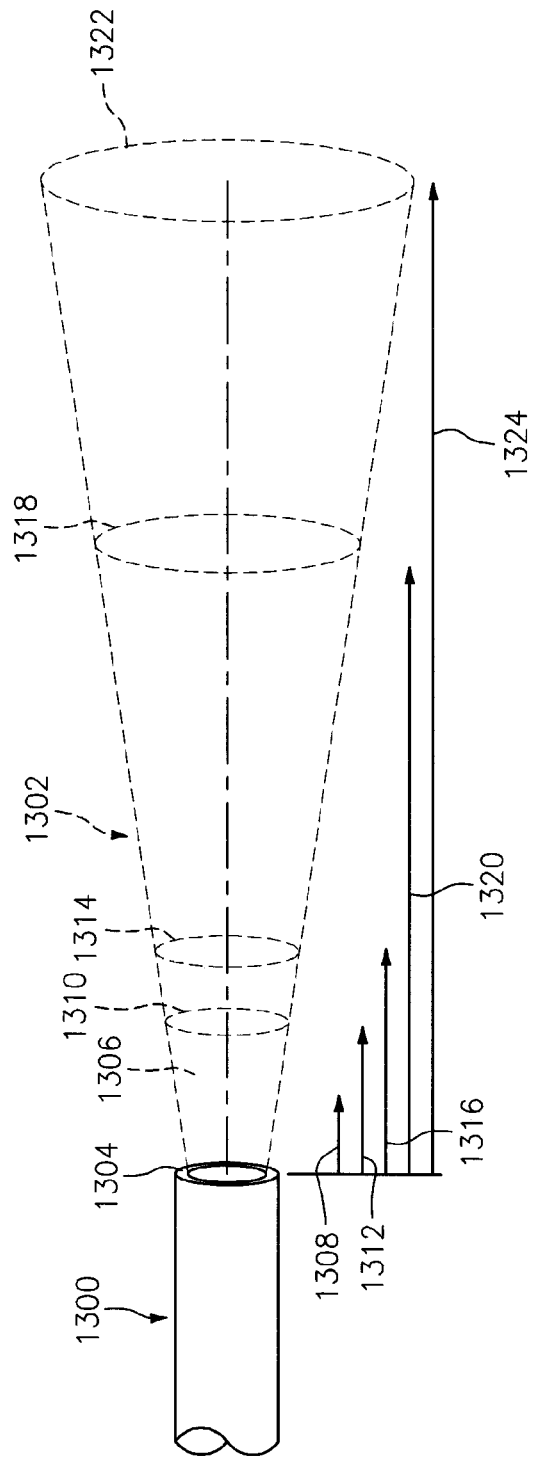
FIG. 14A is an illustration of spot size versus distance to tissue for an energy beam such as a diverging laser beam.

FIG. 14A illustrates a waveguide 1300 for optical radiation including an opto-mechanical system to control the spot size of energy applied to the tissue for a diverging energy beam 1302 coming out of the waveguide 1300. One example is a hollow core fiber currently available from OmniGuide, Inc. that has an inner diameter of approximately 320 microns In one construction, the spot diameter at distal tip 1304 is 320 microns, the spot diameter 1306 at distance 1308 of 1 mm is 400 microns, the spot diameter 1310 at distance 1312 of 2 mm is 485 microns, the spot diameter 1314 at distance 1316 of 3 mm is 570 microns, the spot diameter 1318 at distance 1320 of 2 cm is 2.0 mm, and the spot diameter 1322 at distance 1324 of 3 cm is 2.8 mm.

In one construction, a waveguide tip with a variable cantilevered distal end portion length allows a user to select a spot size, such as by using movable extension 265 in FIGS. 7A and 7B of Anastassiou et al. in U.S. Patent Publication No. 2014/0088577. In another construction, an optical component-type tip such as disclosed by Shurgalin et al. in U.S. Patent Publication No. 2013/0064515 is combined with the movable extension of Anastassiou et al. to adjust spot size and resulting thermal effects during a surgical procedure.

The illustration of the diverging cone 1302, FIG. 14A, of radiation emerging from the waveguide 1300 illustrates how selecting the stand-off distance determines the spot size. The spot size may be determined approximately by directing the laser at a wooden tongue depressor and observing charring of the wood, for example. The spot size for a given waveguide beam divergence may be set during manufacturing, after the product has been sold but before surgery, by the surgical staff, or after or during a procedure. It may be possible to set the stand-off distance once, or many times. The stand-off distance may be set using a push or pull mechanism in the conduit.

The spot size of the laser radiation emitted from the distal tip affects the power density of the laser energy and thereby defines laser tissue interaction, such as cutting or ablation mode, as well as the rate of cutting or ablation. In general, a beam exiting a optical waveguide diverges as shown in FIG. 14A. Therefore, spot size may be controlled by setting a distance between an exit point of the laser radiation and the tissue, i.e., by control of the stand-off distance.

Another way to control the distance between waveguide and the tissue may be by using a proximity sensor built into the waveguide, jacket, or conduit, or in the distal tip of the instrument. This proximity sensor may measure a distance to the tissue and provide a feedback to the user or computer interface. Distance may be controlled by the user or pre-programmed into a computer that automatically maintains a preset distance by adjusting the position of the manipulator.

Figure 15B:
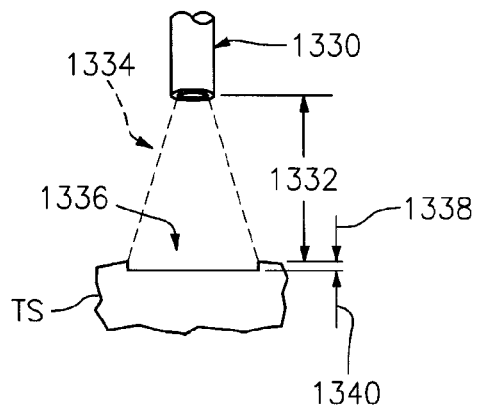
FIGS. 15B and 15C are illustrations of low power and higher power, respectively, with a $CO_2$ laser waveguide spaced relatively far from tissue.
Figure 15D:
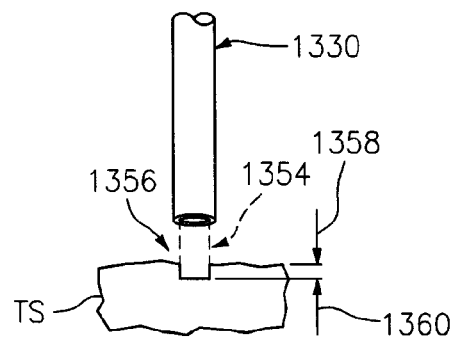
FIGS. 15D and 15E are illustrations of low power and higher power, respectively, with a $CO_2$ laser waveguide spaced relatively close to tissue.
Figure 15C:
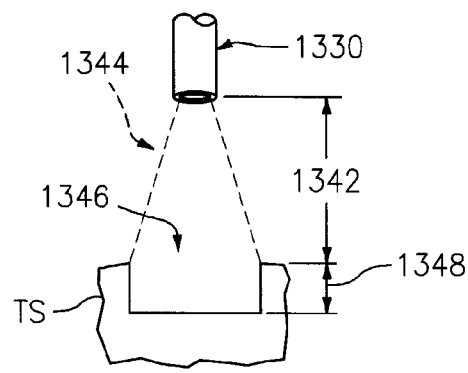

FIGS. 15B and 15C are schematic illustrations of low power and higher power, respectively, with a $CO_2$ laser waveguide 1330 spaced relatively far from tissue. At low power input of 2-4 watts and a distance 1332, FIG. 15B, of 2-3 cm from tissue TS, diverging $CO_2$ laser beam 1334 causes superficial ablation 1336 having a relatively shallow depth as represented by arrows 1338 and 1340. By comparison, at a higher power input of 15-20 watts and a distance 1342, FIG. 15C, of 3-5 cm from tissue TS, diverging $CO_2$ laser beam 1344 causes ablation and coagulation 1346 having a deeper depth as represented by arrow 1348.

Figure 15E:
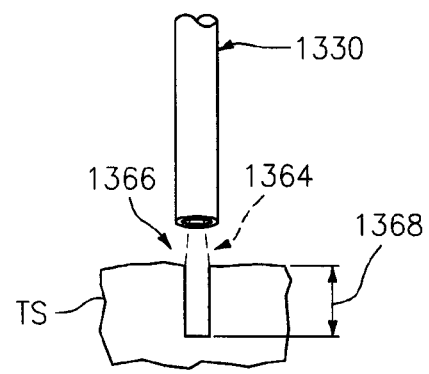

FIGS. 15D and 15E are schematic illustrations of low power and higher power, respectively, with a $CO_2$ laser waveguide 1330 spaced relatively close to tissue TS at a distance of 0.2-0.3 cm in both examples. At a first power input of 6-12 watts, diverging $CO_2$ laser beam 1354, FIG. 15D, causes fine cutting 1356 having a relatively shallow depth as represented by arrows 1358 and 1360. By comparison, at a second, higher power input of 12-20 watts, diverging $CO_2$ laser beam 1364 causes cutting 1366 having a deeper depth as represented by arrow 1368.

Figure 16A:
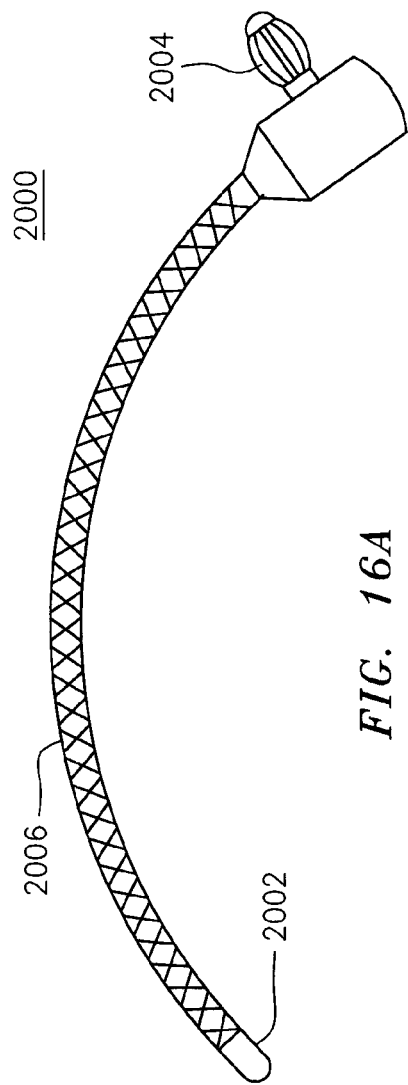
FIGS. 16A and 16B are schematic side views of alternative single-use electrosurgical energy guides for use with a handpiece according to the present invention.
Figure 16B:
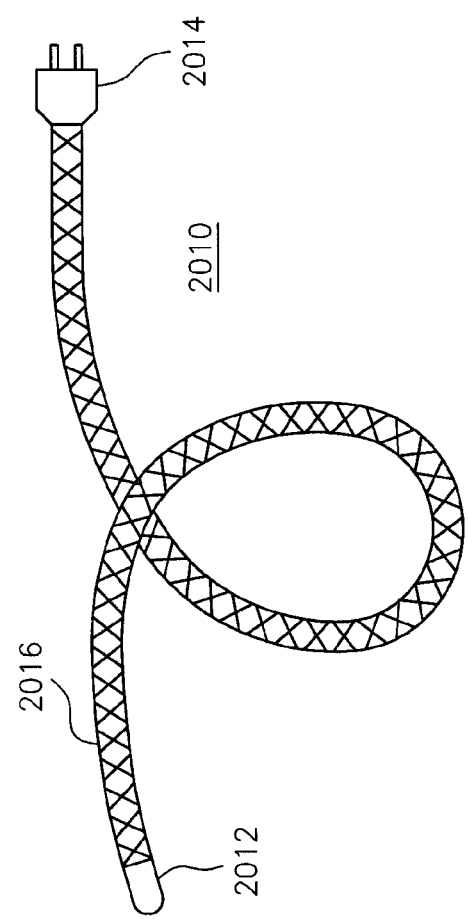

While many of the above-described embodiments involve optical waveguides for laser surgery, this is not a limitation of the invention. Articulating handpieces according to the present invention are also suitable for use with other types of surgical energy such as electrosurgery utilizing microwave or RF energy. FIGS. 16A and 16B are schematic side views of alternative single-use electrosurgical energy guides for use with a handpiece according to the present invention. Guide 2000, FIG. 16A, has an energizable distal tip 2002 electrically connected to a banana plug connector 2004 by an elongated insulated section 2006. Guide 2010, FIG. 16A, has an energizable distal tip 2012 electrically connected to a two-prong plug connector 2014 by an elongated insulated section 2016. Distal tips 2002 and 2012 are insertable through an inner cannula of a handpiece according to the present invention when the distal opening of the handpiece, such as opening 120 shown in FIGS. 7B and 7C, is enlarged to admit the energizable tips therethrough. In other constructions, the inner cannula serves as a working channel or lumen through which mini-laparoscopic instruments such as micro-debriders, cutting tools, forceps, biopsy or drug delivery needles, or other devices preferably having outer diameters less than 5 mm can be utilized as desired.

Figure 17A:
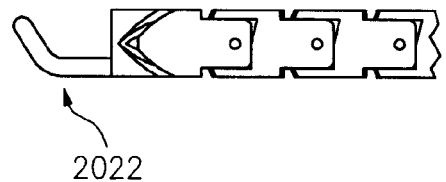
FIGS. 17A-17C are schematic side views of various electrosurgical tips for use according to the present invention.
Figure 17B:
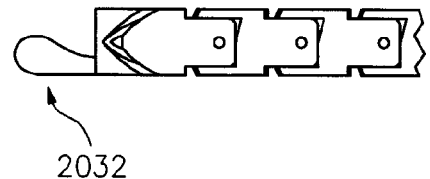
Figure 17C:
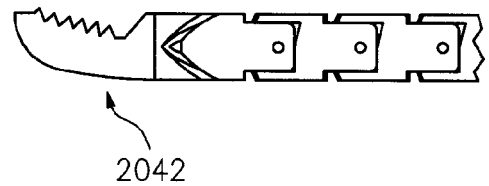

FIGS. 17A-17C are schematic side views of electrosurgical guides having different electrosurgical tips for use according to the present invention. Guide 2020, FIG. 17A, has an L-Hook monopolar electrode 2022. Guide 2030, FIG. 17B, has a spatula monopolar electrode 2032. Guide 2040, FIG. 17C, has a debriding tip 2042, preferably with a rotating tube inside of another tube. In some constructions, tip 2042 is not energized and simply relies on mechanical debridement. In some constructions, one or more links are formed of a dielectric material such as PEEK or other dielectric polymeric material to provide electric insulation as desired.

Figure 18A:
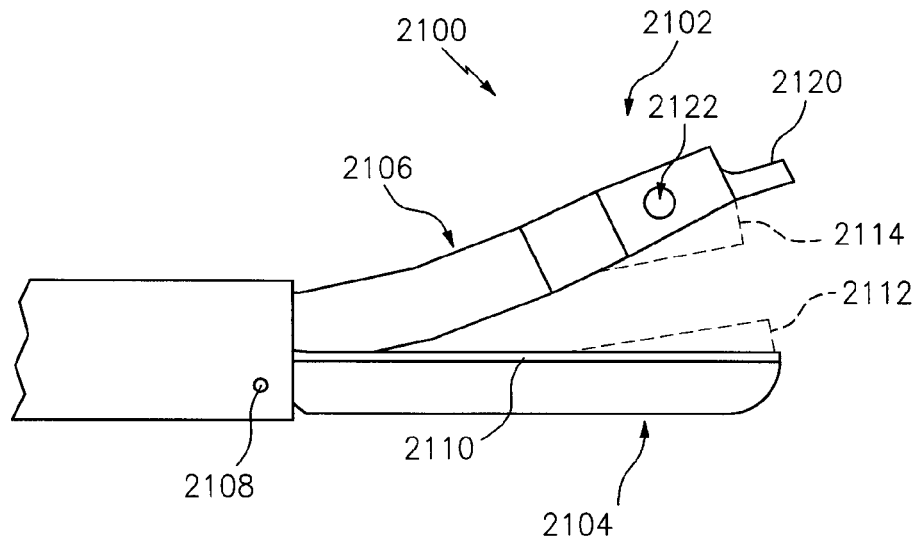
FIGS. 18A-18B are schematic side views of shears added to a distal tip according to the present invention in the open and closed positions, respectively.
Figure 18B:
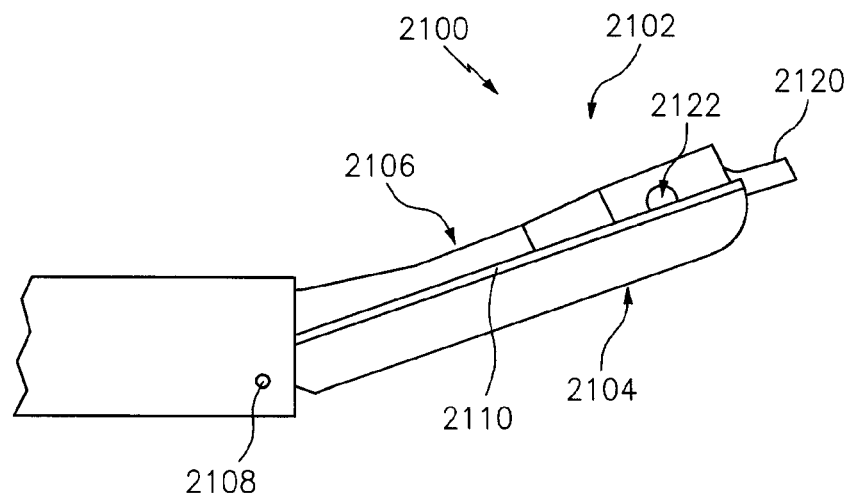

FIGS. 18A and 18B illustrate a distal portion of an instrument 2100 according to the present invention with a cold-cutting, shears-type functionality having a distal tip 2102 that carries at least one moveable jaw 2104 and a second jaw 2106 which is fixed in this construction and terminates in a spatula-type tip 2120 to enhance tissue manipulation and blunt dissection. Movable jaw 2104 pivots about pin 2108 when driven by a proximal pulling force applied to a proximally-extending actuation element, such as a rod or cable attached to a proximal portion (not visible) of jaw 2104; in another construction, a distally-directed pushing force is applied to jaw 2104 by a rod or other drive mechanism. At least one cutting edge 2110 acts as a scissor-type blade when moved past upper jaw 2106. In another construction, both jaws 2104 and 2106 carry cutting blades 2112 and 2114 as indicated by dashed lines in FIG. 18A that meet together when jaw 2104 is driven to the closed position; in yet other constructions, the blades 2112 and 2114 are offset and bypass each other during closure.

In some constructions, surgical energy such as laser energy is delivered as desired when the jaws 2104 and 2106 are in the open, separated position as shown in FIG. 18A. A conduit, such as a single-use waveguide, to conduct surgical energy is positionable within upper jaw 2106 and is visible through a sight hole or viewing port 2122 to confirm full, complete insertion of the waveguide.

Figure 19:
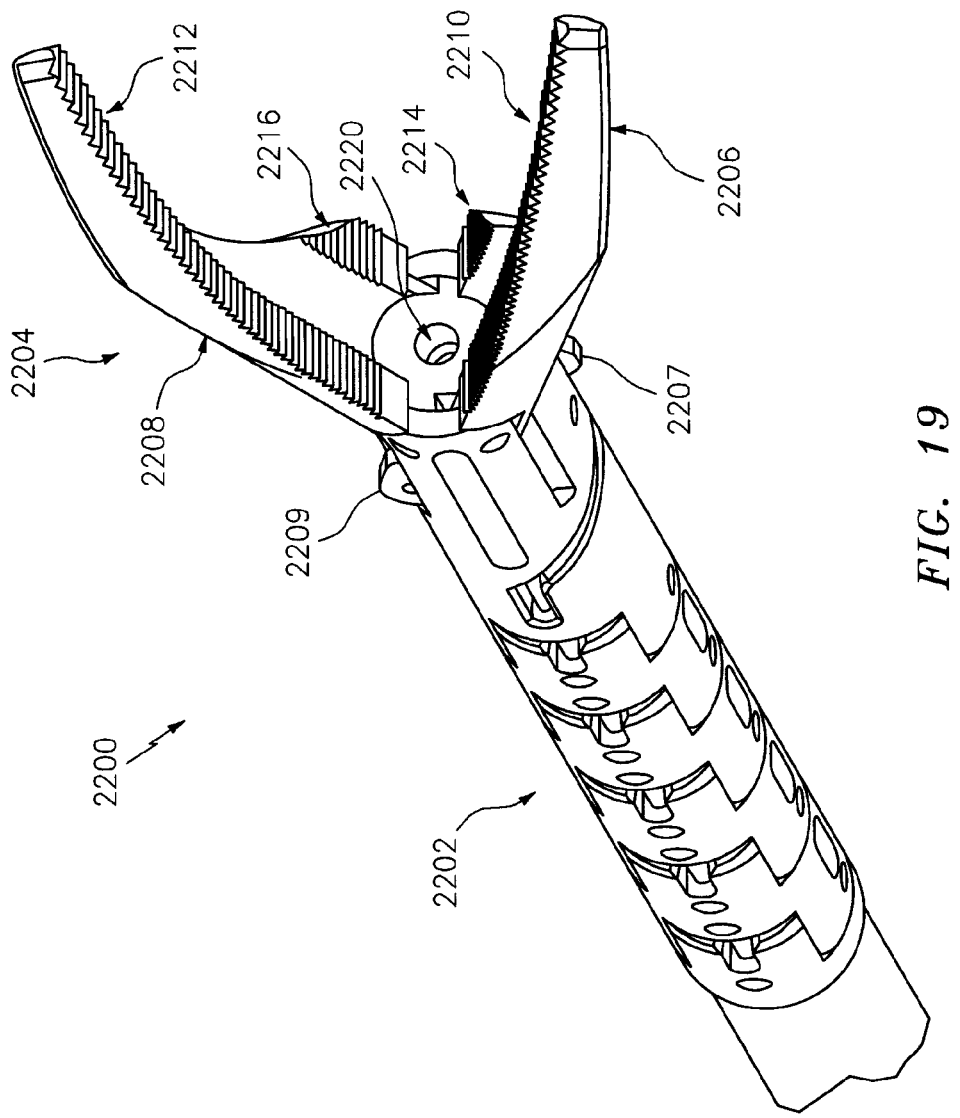
FIG. 19 is a schematic front perspective view of pivotable grasper jaws added to a distal tip according to the present invention.

A still further instrument 2200 according to the present invention is shown in FIG. 19 in an open position with an articulating section 2202 and a distal tip portion 2204 having curved grasper jaws 2206 and 2208. Each jaw 2206, 2208 has teeth disposed on curved grasping surfaces 2210 and 2212, respectively. In this construction, jaws 2206 and 2208 are asymmetric and also have shorter, straight grasping surfaces 2214 and 2216, respectively, which mate together when a driving force is applied to proximal portions 2207 and 2209, respectively, to drive jaws 2206 and 2208 to a closed position. A distal orifice or port 2220 is visible in FIG. 19 through which surgical energy is directed when instrument 2200 is in the open position. In other constructions, different types of tissue manipulation such as debriders or biopsy devices are added to the distal tip unit.

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. An articulating instrument, comprising:
   a handle;
   an articulation actuator having a first portion and a second portion, the articulation actuator coupled to pivotally rotate with respect to the handle about an axis of rotation, the axis of rotation spaced between the first portion and the second portion of the articulation actuator, the first and the second portions of the articulation actuator each exposed to physical contact to be physically manipulable to operate the articulating instrument;
   a distal assembly having a proximal end, a distal end, a length that extends between the proximal end and the distal end, a lumen that extends between the proximal end and the distal end, and at least one passage that extends between the proximal end and the distal end, the distal assembly comprising a plurality of links successively arranged along at least a portion of the length of the distal assembly, successive ones of the links pivotally coupled to a respective previous one of the links to articulate between a first configuration, a second configuration, and a plurality of intermediate configurations between the first and the second configurations, the second configuration in which the distal assembly is curved at a maximum articulation angle, the intermediate configurations in which the distal assembly is curved at a respective articulation angle, the respective articulation angles each of which is smaller than the maximum articulation angle;
   and at least one actuation member having a first leg and a second leg, each of the first leg and the second leg having a proximal end and a distal portion and which passes through the at least one passage of the distal assembly, the proximal ends of the first leg and the second leg coupled to the articulation actuator to move in response to a pivotal rotation of the articulation actuator and the distal portion that physically engages at least a portion of the distal assembly to adjust a tension applied thereto in response to the pivotal rotation of the articulation actuator, the proximal end of the first leg movable between a first position in which the first leg perpendicularly intersects the axis of rotation and a second position in response to rotation of the articulation actuator in a first rotational direction, the proximal end of the second leg movable between the first position in which the second leg perpendicularly intersects the axis of rotation and a third position in response to rotation of the articulation actuator in a second rotational direction opposite the first rotational direction, wherein the articulation actuator includes a number of stops, the links each include a respective number of stops, and the stops of the links engage before the stops of the articulation actuator engage to render at least one of the first and the second configurations relatively more stable than the intermediate configurations such that the distal assembly has a tendency to remain in the first or the second configurations when placed in the at least one of the first or the second configurations.

2. The instrument of claim 1, further comprising:
a cannula portion positioned between the distal assembly and the handle, wherein the distal assembly terminates in a distal tip unit and the plurality of pivotally coupled links connect the cannula portion to the distal tip unit.

3. The instrument of claim 2 wherein the first and the second legs extend through the cannula portion and through the distal assembly.

4. The instrument of claim 2 wherein the at least one actuation member comprises a cable having a central portion passing through the distal tip unit, the cable including the first leg and the second leg which extend from respective ends of the central portion, the first and the second legs which extend proximally through respective ones of the passages of the distal assembly and through the cannula portion, the proximal ends of the first and the second legs connected to the articulation actuator.

5. The instrument of claim 4 wherein the articulation actuator is pivotal between a first terminal position and a second terminal position, the first and the second terminal positions defined by respective ones of the stops of the articulation actuator to limit motion about the rotational axis in each of the first rotational direction and the second rotational direction.

6. The instrument of claim 5 wherein rotation of the articulation actuator simultaneously increases a tension on one of the first and second legs while releasing a tension on the other of the first and the second legs.

7. The instrument of claim 5 wherein rotation of the articulation actuator to the first terminal position increases tension on the first leg while simultaneously ensuring that no tension is placed on the second leg by the articulation actuator.

8. The instrument of claim 7 wherein the central portion of the cable is fixedly attached to the distal tip unit.

9. The instrument of claim 2 wherein the distal tip unit includes at least one marking or opening to assist at least one of aiming and orientation of the distal tip unit.

10. The instrument of claim 2, further comprising a conduit that extends through the handle, the cannula portion, and the distal assembly to emit surgical energy through the distal tip unit to a target location.

11. The instrument of claim 10, further comprising an energy source operable to provide at least a first surgical energy to the conduit.

12. The system of claim 11 wherein the energy source is a source of optical electromagnetic radiation and the conduit is a removable waveguide optically coupled to receive the optical electromagnetic radiation from the energy source.

13. The instrument of claim 1 wherein the distal assembly comprises at least one distal tissue manipulation feature.

14. The instrument of claim 13 wherein the at least one the distal tissue manipulation feature includes at least one projecting feature that extends from the distal tip unit.

15. The instrument of claim 13 wherein the at least one distal tissue manipulation feature is adapted to at least one of a cutting feature, a debriding feature, a grasping feature, or blunt dissection feature.

* * * * *